US00RE39608E

(19) United States
(12) Reissued Patent
Lubisch et al.

(10) Patent Number: US RE39,608 E
(45) Date of Reissued Patent: May 1, 2007

(54) SUBSTITUTED BENZIMIDAZOLES AND THEIR USE AS PARP INHIBITORS

(75) Inventors: Wilfried Lubisch, Heidelberg (DE); Michael Kock, Schifferstadt (DE); Thomas Höger, Laudenbach (DE); Sabine Schult, Speyer (DE); Roland Grandel, Dossenheim (DE); Reinhold Müller, Schifferstadt (DE)

(73) Assignee: Abbott GmbH & Co. KG, Wiebaden (DE)

(21) Appl. No.: 10/935,683

(22) PCT Filed: Nov. 23, 1999

(86) PCT No.: PCT/EP99/09004

§ 371 (c)(1),
(2), (4) Date: May 24, 2001

(87) PCT Pub. No.: WO00/32579

PCT Pub. Date: Jun. 8, 2000

Related U.S. Patent Documents

Reissue of:
(64) Patent No.: 6,448,271
Issued: Sep. 10, 2002
Appl. No.: 09/856,686
Filed: May 24, 2001

(30) Foreign Application Priority Data

Nov. 27, 1998 (DE) ..... 198 54 933
Apr. 12, 1999 (DE) ..... 199 16 460

(51) Int. Cl.

| | |
|---|---|
| ***A61K 31/4184*** | (2006.01) |
| ***A61K 31/454*** | (2006.01) |
| ***C07D 401/04*** | (2006.01) |
| ***C07D 401/14*** | (2006.01) |
| ***C07D 403/02*** | (2006.01) |

(52) U.S. Cl. ..... 514/322; 514/211.08; 514/253.09; 514/254.06; 514/316; 514/394; 540/575; 544/364; 544/370; 546/187; 546/199; 548/306.1

(58) Field of Classification Search ..... 548/306.1; 546/187, 199; 544/364, 370; 540/575; 514/211.08, 514/253.09, 254.06, 316, 322, 394
See application file for complete search history.

(56) References Cited

U.S. PATENT DOCUMENTS

| | | | |
|---|---|---|---|
| 4,093,726 | A | 6/1978 | Winn et al. |
| 5,830,905 | A | 11/1998 | Diana et al. |
| 5,877,187 | A | 3/1999 | Orjales et al. |
| 5,958,950 | A | 9/1999 | Padia et al. |
| 5,972,980 | A | 10/1999 | Cornicelli et al. |
| 6,001,866 | A | 12/1999 | Cornicelli et al. |
| 6,127,384 | A | 10/2000 | Diana et al. |
| 6,303,627 | B1 | 10/2001 | Koch et al. |

FOREIGN PATENT DOCUMENTS

| | | |
|---|---|---|
| DE | 1354554 | 8/1971 |
| WO | WO 97/04771 | 2/1997 |
| WO | WO 98/33802 | 8/1998 |

OTHER PUBLICATIONS

Wahlgren, Curtis G. and Addison, Anthony W., Synthesis of Some Benzimidazole–, Ryridine– and Imidazole–Derived Chelating Agents, J. Heterocylic Chem., 26, 541 (1989), May–Jun. 1989, Chemistry Dept., Drezel University, Philadelia, PA.

Denny, William A., Newcastle, Gordon W. and Baguley, Bruce C., Potential Antitumor Agents. 59. Structure–Activity Relationships for 2–Phenylbenzimidazole–4–carboxamides, a New Class of "Minimal" DNA–Intercalating Agents Which May Not Act via Topoisomerase II, J. Med. Chem., 1990, vol. 33. No. 2, 815–819, University of Auckland School of Medicine, Auckland, New Zealand.

Orjales, Aurelio, Bordell, Maravillas and Rubio, Victor, Synthesis and Structure Activity Relationship of New Piperidinyl and Piperazinyl Derivatives as Antiallergics, J. Heterocylic Chem. 32, 707 (1995), Research Dept., FAES S.A. Bilboa, Spain.

Zarins, P., Lavinovich, E.S.; Arens, A and Germane, S., Abstract Substituted Piperidines were prepared by condensing piperidinecarboxylic acid with the corresponding o–HZC6H4NH2 at 220–50. degree. in polyphosphoric acid. Institute of Organic Synthesis, Academy of Sciences, Latvia S.S.R. U.S.S.R; CA 80: 146143, 1974.

(Continued)

*Primary Examiner*—Laura L. Stockton
(74) *Attorney, Agent, or Firm*—Wood, Phillips, Katz, Clark & Mortimer

(57) ABSTRACT

Compounds of the formula Ia or IB

Ia

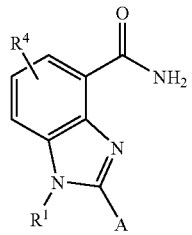

Ib

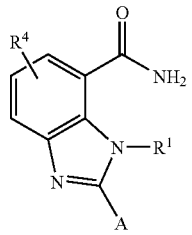

where

A is a saturated or monounsaturated heterocyclic, 4 - to 8-membered ring which contains one or two nitrogen atoms, and their tautomeric forms, possible enantiomeric and diastereomeric forms, their prodrugs and possible physiologically tolerated salts are useful as inhibitors of the enzyme poly(ADP-ribose)polymerase.

40 Claims, No Drawings

OTHER PUBLICATIONS

Zarin, P.P., Lavrinovich, E.S. and Aren, A.K., Pyridinium Salts I. Reduction of 4–(Benzazol–2–yl) Pyridinium Salts in a Neutral Medium, UDC 547.821.3:547–822.1, Institute of Organic Synthesis, Academny of Sciences of the Latvian SSH, Riga. Jan., 1974.

Iemura, R., Kawashima, T., Fukuda, T., ITO, K. and Tsukamoto, T., Synthesis of Zensimidazole Derivatives as Potential $H_1$–Antihistaminic Agents, J. Heterocyclic Chem. 24, 31 (1987), Jan.–Feb. 1987, Pharmaceuticals Reserach Center, Kanebo Ltd., 5–90, Tomobuchi–cho 1–Chome, Miyakojima–ku, Osaka, 534, Japan.

SUBSTITUTED BENZIMIDAZOLES AND THEIR USE AS PARP INHIBITORS

Matter enclosed in heavy brackets [ ] appears in the original patent but forms no part of this reissue specification; matter printed in italics indicates the additions made by reissue.

This application is a 371 of PCT/EP99/09004 filed Nov. 23, 1999.

The present invention relates to novel benzimidazoles, their preparation and their use as inhibitors of the enzyme poly(ADP-ribose)polymerase or PARP (EC 2.4.2.30) for the preparation of drugs.

Poly(ADP-ribose)polymerase (PARP) or, as it is also known, poly(ADP-ribose)synthase (PARS) is a regulatory enzyme which is found in cell nuclei (K. Ikai et al., J. Histochem. Cytochem. 31 (1983), 1261–1264). It is assumed that PARP plays a role in repairing DNA breaks (M. S. Satoh et al., Nature 356 (1992), 356–358). Damage to or breaks in the DNA strands activate the enzyme PARP which, if it has been activated, catalyses the transfer of ADP-ribose from NAD (S. Shaw, Adv. Radiat.Biol. 11 (1984), 1–69). Nicotinamide is liberated from NAD. Nicotinamide is converted back into NAD with consumption of the energy carrier ATP by other enzymes. Overactivation of PARP would accordingly result in an unphysiologically high consumption of ATP, and this leads to cell damage and cell death in extreme cases.

It is known that radicals such as the superoxide anion, NO and the hydrogen peroxide can lead to DNA damage in cells and hence activate PARP. The formation of large amounts of radicals is observed in a number of pathophysiological conditions, and it is assumed that this accumulation of radicals leads or contributes to the observed cell or organ damage. These include, for example, ischemic conditions of organs, as in stroke, myocardial infarct (C. Thiemermann et al., Proc. Natl. Acad. Sci USA 94 (1997), 679–683) or ischemia of the kidneys, as well as reperfusion damage as occurs, for example, following the lysis of myocardial infarct (see above: C. Thiermermann et al.). The inhibition of the enzyme PARP might accordingly be a means for preventing or reducing this damage at least in part. PARP inhibitors might therefore constitute a new therapeutic principle for treating a number of disorders.

The enzyme PARP influences the repair of DNA damage and could thus also play a role in therapy of cancer diseases, since the higher action potential against tumor tissue was observed in combination with cytostatic substances (G. Chen et al. Cancer Chemo. Pharmacol. 22 (1988), 303).

Nonlimiting examples of tumors are leukemia, glioblastomas, lymphomas, melanomas, carcinomas of the breast and cervical carcimonas. It was also found that PARP inhibitors can have an immunosuppressive effect (D. Weltin et al. Int. J. Immunopharmacol. 17 (1995), 265–271).

It was also discovered that PARP is involved in immunological diseases or disorders in which the immune system plays an important role, for example rheumatoid arthritis and septic shock, and that PARP inhibitors can have an advantageous effect on the course of the disorder (H. Kröger et al. Inflammation 20 (1996), 203–215; W. Ehrlich et al. Rheumatol. Int. 15 (1995), 171–172; C. Szabo et al., Proc. Natl. Acad. Sci. USA 95 (1998), 3867–3872; S. Cuzzocrea et al. Eur. J. Pharmacol. 342 (1998), 67–76).

For the purposes of this invention, PARP is also understood as meaning isoenzymes of the PARP enzyme described above.

Furthermore, the PARP inhibitor 3-aminobenzamide exhibited protective effects in a model for circulatory shock (S. Cuzzocrea et al., Br. J. Pharmacol. 121 (1997), 1065–1074).

PARP is also involved in diabetes mellitus (V. Burkhart et al., Nature Medicine (1999), 5314–19).

Benzimidazoles have been widely described.

The synthesis of 2-phenylbenzimidaz-4-ylamides which also carry a substituted alkyl chain on the amide radical and which are said to have a cytotoxic effect is mentioned in J. Med. Chem. 33 (1990), 814–819. WO 97/04771 mentions 4-benzimidazolamides which inhibit PARS. In particular, derivatives which carry a phenyl ring in the 2-position, where the phenyl ring may furthermore be substituted by simple substituents such as nitro, methoxy or $CF_3$, are described there as being effective. Although some of these substances exhibit good inhibition of the enzyme PARP, the derivatives described there have the disadvantage that they have little or no solubility in aqueous solutions and hence cannot be applied as an aqueous solution.

Benzimidazoles which carry a piperidine ring in the 2-position have also been described. Thus, in J. Het. Chem. 24 (1987), 31, derivatives have been prepared as antihistamine drugs. In J. Het. Chem. 32 (1995), 707 and J. Het. Chem. 26 (1989), 541, analogous compounds having the same use have been described. 2-Piperidinylbenzimidazoles are mentioned in EP 818454 as antihistamine drugs and in WO 9736554 as agents against hepatitis. Derivatives are likewise mentioned in CA 80, 146143, Fr. 2103639 and in Khim. Ceterotsikl. Soedin 1 (1974), 104.

However, the importance of substituents on the phenylaromatics in the benzimidazole fragment has not been investigated. Furthermore, those benzimidazoles which carry a 4- to 8-membered heterocycle, in particular a piperidine ring, in the 2-position have not been described to date as being PARP inhibitors.

The present application describes the surprising finding that the introduction of a carboxamide radical on the benzimidazole aromatic gives benzimidazoles which constitute novel and highly effective PARP inhibitors, provided that they are substituted in the 2-position by a saturated heterocycle.

In a number of treatments, such as for stroke, the active compounds are applied intravenously as an infusion solution. For this purpose, it is necessary to have substances, in this case PARP inhibitors, which have sufficient water solubility at or about physiological pH (i.e. pH of 5–8), so that an infusion solution can be prepared. However, many of the PARP inhibitors described, in particular the more effective PARP inhibitors, have the disadvantage that they exhibit only little or no water solubility at the pH values and are therefore not suitable for intravenous application. Such active compounds can be applied only with excipients which are intended to impart water solubility (cf. WO 97/04771). These excipients, for example polyethylene glycol and dimethyl sulfoxide, frequently cause side effects or are even not tolerated. No highly effective PARP inhibitors having sufficient water solubility have been described to date.

It was surprisingly found that benzimidazoles which carry a piperidine ring on the imidazole ring are highly effective inhibitors and, owing to the incorporating of the aliphatic amine radical, permit salt formation with acids, resulting in substantially improved water solubility and hence permitting the preparation of an infusion solution.

The present invention describes novel benzimidazole derivatives of the formula I which have advantages over the compounds described above and constitute potent PARP inhibitors and at the same time have sufficient water solu bility. When compounds of the formula I are referred to, they are understood as meaning the compounds of the formulae Ia and Ib. The present invention relates to substituted benzimidazoles of the formula I:

Ia

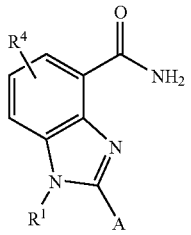

Ib

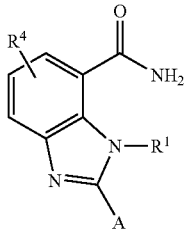

where $R^1$ is hydrogen or branched or straight-chain $C_1$–$C_6$-alkyl, where one carbon atom of the alkyl radical may furthermore carry $OR^5$ (where $R^5$ is hydrogen or $C_1$–$C_4$-alkyl), or one carbon atom in the chain may also carry an =O group or a group $NR^8R^9$, where $R^8$ and $R^9$, independently of one another, are each hydrogen or $C_1$–$C_4$-alkyl and $NR^8R^9$ together may be a cyclic amine having 4 to 8 ring atoms, where the carbon chains in $R^8$ or $R^9$ or the ring formed by $NR^8R^9$ may furthermore carry a radical $R^6$ which, independently of $R^2$, may have the same meaning as $R^2$, $R^4$ is hydrogen, branched or straight-chain $C_1$–$C_6$-alkyl, chlorine, bromine, fluorine, nitro, cyano, $NR^8R^9$, NH—CO—$R^{10}$ or $OR^8$, where $R^8$ and $R^9$, independently of one another, are each hydrogen or $C_1$–$C_4$-alkyl and $NR^8R^9$ together may be a cyclic amine having 4 to 8 ring atoms, where the ring may furthermore carry a radical (branched or straight-chain $C_1$–$C_6$-alkyl, $C_3$–$C_7$-cycloalkyl-$C_1$–$C_4$-alkyl, CO—$R^{41}$, $COOR^{41}$ or phenyl), and $R^{10}$ may be hydrogen, $C_1$–$C_4$-alkyl or phenyl and $R^{41}$ may have the same meanings as $R^{21}$, A is a saturated or monounsaturated heterocyclic 4- or 8-membered ring which contains one or two nitrogen atoms and, optionally, an oxygen or sulfur atom, which ring is substituted by $R^2$ and $R^3$, where $R^2$ is hydrogen, branched or straight-chain $C_1$–$C_8$-alkyl which may furthermore by substituted by $R^{23}$, and a carbon atom of the chain may carry an =O group, $C_3$–$C_7$-cycloalkyl-$C_1$–$C_4$-alkyl, —CO—$(NH)_{0.1}$—$R^{21}$, $COOR^{21}$ or phenyl, where $R^{21}$ is hydrogen, branched or straight-chain $C_1$–$C_6$-alkyl, $C_3$–$C_7$-cycloalkyl-$C_1$–$C_4$-alkyl, phenyl-$C_1$–$C_4$-alkyl, $C_3$–$C_7$-cycloalkyl or phenyl, and each radical may furthermore carry $(CH_2)_{0-2}$—$R^{23}$ and the respective phenyl ring in turn may furthermore be substituted by 1, 2 or 3 of the following radicals: chlorine, fluorine, bromine, iodine, branched and straight-chain $C_1$–$C_4$-alkyl, nitro, $CF_3$, cyano, —$(CH_2)_{0-2}$—$NR^{24}R^{25}$, NH—CO—$R^{10}$, $OR^{10}$, $COOR^{10}$, $SO_2$—$C_1$–$C_4$-alkyl, $SO_2Ph$, $SO_2NH$, $NHSO_2$—C1–$C_4$-alkyl, $NHSO_2Ph$ and $CF_3$, where $R^{24}$ and $R^{25}$, independently of one another, are each hydrogen or $C_1$–$C_4$-alkyl and $NR^{24}R^{25}$ together may be a cyclic amine having 4 to 8 ring atoms, where the ring may furthermore carry a radical of branched or straight-chain $C_1$–$C_6$-alkyl, $C_3$–$C_7$-cycloalkyl-$C_1$–$C_4$-alkyl, CO—$R^{22}$, $COOR^{22}$ (where $R^{22}$ is hydrogen, branched or straight-chain $C_1$–$C_6$-alkyl, $C_3$–$C_7$-cycloalkyl-$C_1$–$C_4$-alkyl, phenyl-$C_1$–$C_4$-alkyl, $C_3$–$C_7$-cycloalkyl or phenyl) or phenyl, and $R^{10}$ is hydrogen, $C_1$–$C_4$-alkyl or phenyl, and $R^{23}$ is $NR^{26}R^{27}$ where $R^{26}$ and $R^{27}$ are each hydrogen, $C_1$–$C_6$-alkyl, $C_0$–$C_4$-alkylphenyl, where the phenyl ring may furthermore be substituted by up to 3 radicals Cl, F, Br, I, $C_1$–$C_4$-alkyl, $CF_3$, CN, $SO_2$—$C_1$–$C_4$-alkyl, $SO_2$-phenyl, $NO_2$, $NH_2$, NHCO—$C_1$–$C_4$-alkyl, NHCO-phenyl, OH, O—$C_1$–$C_4$-alkyl, O—$C_1$–$C_4$-alkylphenyl, and $NR^{26}R^{27}$ may also be a cyclic amine having 3 to 8 members, where a further hetero atom such as O, N and S may also additionally be present, and the ring may furthermore be substituted by a radical $R^{28}$ where $R^{28}$ may be $C_1$–$C_4$-alkyl and $C_1$–$C_4$-alkylphenyl, $R^3$ is hydrogen, branched or straight-chain $C_1$–$C_6$-alkyl, $C_3$–$C_7$-cycloalkyl-$C_1$–$C_4$-alkyl which is unsubstituted or substituted by $C_1$–$C_6$-alkyl or $C_3$–$C_7$-cycloalkyl which is unsubstituted or substituted by $C_1$–$C_6$-alkyl, where one carbon atom of the radical may furthermore carry a phenyl ring which in turn may also be substituted by 1, 2 or 3 of the following radicals: chlorine, fluorine, bromine, iodine, branched and straight-chain $C_1$–$C_4$-alkyl, nitro, $CF_3$, cyano, $(CH_2)_{0-2}$—$NR^{32}R^{33}$, NH—CO—$R^{10}$, $OR^{10}$, $COOR^{10}$, $SO_2$—$C_1$–$C_4$-alkyl, $SO_2Ph$, $CH_3$, $SO_2NH$, $NHSO_2$—$C_1$–$C_4$-alkyl, $NHSO_2Ph$ and $CF_3$, where $R^{32}$ and $R^{33}$, independently of one another, are each hydrogen or $C_1$–$C_4$-alkyl and $NR^{32}R^{33}$ together may be a cyclic amine having 4 to 8 ring atoms, where the ring may furthermore carry a radical of branched or straight-chain $C_1$–$C_6$-alkylm $C_3$–$C_7$-cycloalkyl-$C_1$–$C_4$-alkyl, CO—$R^{31}$, $COOR^{31}$ or phenyl, and $R^{10}$ is hydrogen, $C_1$–$C_4$-alkyl or phenyl, and $R^{31}$ may have the same meaning as $R^{21}$, and their tautomeric forms, possible enantiomeric and diastereomeric forms, their prodrugs and possible physiologically tolerated salts.

The compounds of the formula I where $R^1$ is hydrogen are preferred.

The compounds of the formula I where $R^2$ is hydrogen are preferred.

The compounds of the formula I where $R^4$ is hydrogen are preferred.

The compounds of the formula I where $R^3$ is hydrogen are preferred.

The compounds of the formula I where $R^3$ is hydrogen, $C_1$–$C_6$-alkyl, benzyl or phenethyl are preferred.

The compounds of the formula I where $R^1$, $R^2$ and $R^4$ are each hydrogen and A is piperidine which is bonded at the 4-position on the benzimidazole and $R^3$ is hydrogen, $C_1$–$C_6$-alkyl, benzyl or phenethyl and is bonded in the 1-position on the piperidine ring are particularly preferred.

The respective meanings of $R^5$ to $R^{10}$ are independent of one another in $R^1$ to $R^4$.

The preferred meanings of $NR^8R^9$, $NR^{24}R^{25}$ and $NR^{32}R^{33}$, as cyclic amine, are piperidine, pyrrolidine, piperazine and homopiperazine. In the case of piperazine and homopiperazine, the ring may preferably furthermore carry a radical of branched or straight-chain $C_1$–$C_6$-alkyl, $C_3$–$C_7$-cycloalkyl-$C_1$–$C_4$-alkyl, CO—$R^7$ or phenyl.

The preferred meaning of A is piperidine, pyrrolidine, piperazine, morpholine or homopiperazine.

The compounds of the formula I where A is piperazine or piperidine are particularly preferred.

The compounds of the formula I may be used in the form of racemates, enantiomerically pure compounds or diastereomers. If enantiomerically pure compounds are desired, these can be obtained, for example, by carrying out a classical resolution of the racemate with the compounds of the formula I or their intermediates used in a suitable optically active base or acid.

The saturated or monounsaturated cyclic structures A may be present as cis-isomers, trans-isomers or mixtures thereof.

The present invention also relates to compounds which are mesomers or tautomers of compounds of the formula I.

The present invention furthermore relates to the physiologically tolerated salts of the compound I, which can be obtained by reacting compounds I with a suitable acid or base. Suitable acids and bases are listed, for example, in Fortschritte der Arzneimittelforschung, 1966, Birkhäuser Verlag, Vol. 10, pages 224–285. These include, for example, hydrochloric acid, citric acid, tartaric acid, lactic acid, phosphoric acid, methanesulfonic acid, acetic acid, formic acid, maleic acid, fumaric acid, etc., and sodium hydroxide, lithium hydroxide, potassium hydroxide and Tris.

Prodrugs are understood as meaning those compounds which are metabolized in vivo to give compounds of the formula I. Typical prodrugs are phosphates, carbamates of amino acids, esters and others.

The preparation of the novel benzimidazoles I can be carried out by various routes which are shown in synthesis scheme 1.

Synthesis Scheme 1

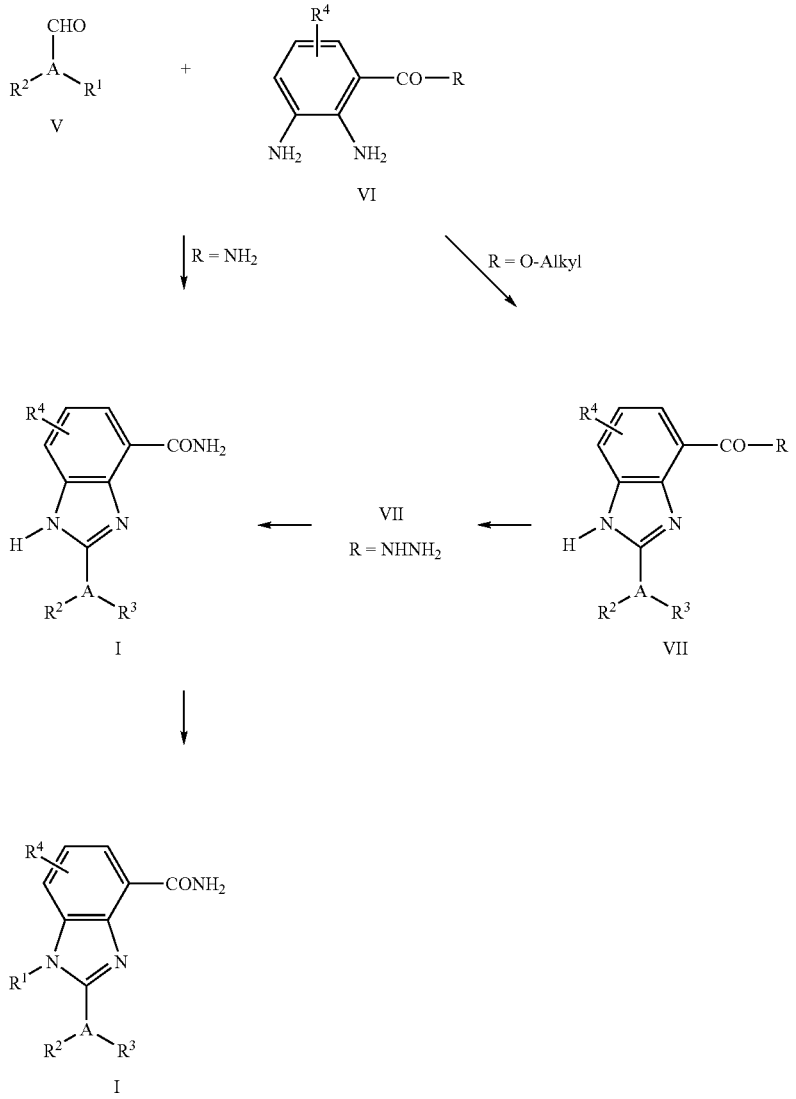

The benzimidazole I or VII is obtained by condensation of the aldehyde V with phenylenediamines V1, the procedure preferably being carried out in polar solvents, such as ethanol or dimethylformamide, and with the addition of acids, such as acetic acid, at elevated temperatures, as a rule from 80 to 120° C. It is advantageous for the reaction to add weak oxidizing agents, such as copper(II) salts, which are added as aqueous solution.

Synthesis Scheme 2

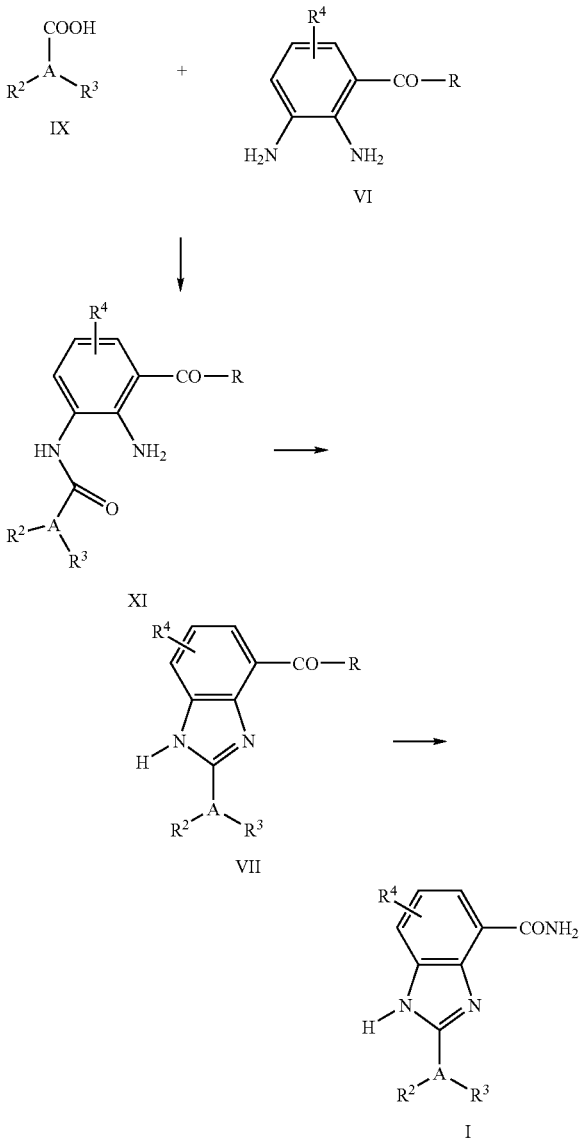

If, in the benzimidazole VII, R is $NH_2$, novel compounds I are formed directly in the condensation. Otherwise, if R is O-alkyl these esters can be reacted with ammonia, if required at elevated temperatures and superatmospheric pressure, to give the amide I. Alternatively, the esters VII can be reacted with hydrazine in polar solvents, such as the alcohols butanol and ethanol or dimethylformamide, at elevated temperatures, preferably from 80 to 130° C., the result being hydrazide VII (R=$NHNH_2$) which can then be reduced under reductive conditions, for example with Raney nickel in alcohols under reflux, to give the amide I.

The radical $R^1$ on the benzimidazole radical in I ($R^1$=H) is introduced under conventional alkylating conditions. Benzimidazoles I are alkylated with $R^1$—L, where L is a leaving group, using a base at from 25 to 150° C., but mainly at elevated temperatures such as from 60 to 130° C., the novel product I where $R^1$≈hydrogen being obtained. The procedure is carried out in solvents, for example dimethylformamide, dimethylsulfoxide, alcohols, e.g. ethanol, ketones, e.g. methyl ethyl ketone or acetone, aliphatic ethers, e.g. tetrahydrofuran, and hydrocarbons, e.g. toluene, it also being possible to use mixtures. Suitable bases are, for example, alcoholates, e.g. sodium ethanolate and potassium tert-butanolate, carbonates, e.g. potassium carbonate, hydrides, e.g. sodium hydride, and hydroxides, e.g. sodium hydroxide and potassium hydroxide.

Various crown ethers, such as 18-crown-6, may also be added in catalytic amounts. Phase transfer conditions may also be employed (for methods, cf. R. C. Larock, Comprehensive Organic Transformations, 1989, page 445 et seq.). The leaving group L used may be a halide, e.g. bromide, chloride or iodide, or, for example, a tolysate or mesylate.

Synthesis Scheme 3

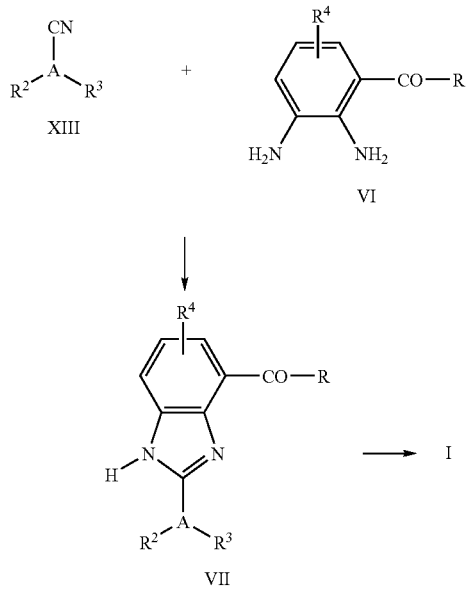

Alternatively to the aldehydes V shown in Scheme 1 it is also possible to use benzoic acids, such as IX (cf. Scheme 2), or benzonitriles, such as XIII (cf. Scheme 3), instead of the benzaldehyde. The preparation of these derivatives is carried out analogously to the preparation of the substituted benzaldehydes V. Starting from IX, the condensation to give VII is carried out in two stages. First, the benzoic acid XI is reacted with the aniline VI with a peptide-like coupling to give the amide XII. The conditions used here are the conventional ones which are listed, for example, in Houben-weyl, Methoden der Organischen Chemie, $4^{th}$ Edition, E5, Chapter V, or C. R. Larock, Comprehensive Organic Transformations, VCH Publisher, 1989, page 972 et seq. Cyclization to the benzimidazole is then effected at elevated temperatures, for example from 60 to 180° C., with or without solvents, such as dimethylformamide, with the addition of acids, such as acetic acid, or directly in acetic acid itself.

The reaction of the phenylenediamine VI with a benzonitrile XIII is likewise effected under conventional conditions. It is possible to employ solvents, such as dimethylformamide, with the addition of acids at elevated temperatures, such as from 60 to 200° C. However, it is also possible to use the conventional methods for the preparation of amides from benzonitriles, as described in J. Amer. Chem. Soc. (1957), 427 and J. Org. Chem. (1987), 1017.

The substituted benzimidazoles I contained in the present invention are inhibitors of the enzyme poly(ADP-ribose) polymerase or PARP (EC 2.4.2.30).

The inhibitory effect of the substituted benzimidazoles I was determined by an enzyme test already known in the literature, the $K_i$ value being determined as a measure of activity. The benzimidazoles I were measured in this way for an inhibitory effect of the enzyme poly(ADP-ribose) polymerase or PARP (EC 2.4.2.30).

The substituted benzimidazoles of the formula I are inhibitors of poly(ADP-ribose) polymerase (PARP) or, as it is also referred to, poly(ADP-ribose)synthase (PARS) and can therefore be used for the treatment and prophylaxis of disorders which are associated with increased activity of these enzymes.

The compounds of the formula I can be used for preparing drugs for the treatment of damage following ischemias and for prophylaxis where ischemias of various organs are expected.

The present benzimidazoles of the formula I can then be used for the treatment and prophylaxis of neurodegenerative disorders which occur after ischemia, trauma (craniocerebral trauma), massive bleeding, subarachnoid hemorrhages and stroke, and of neurodegenerative disorders such as multi-infarct dementia. Alzheimer's disease and Huntington's disease and of epilepsies, in particular of generalized epileptic attacks, for example petit mal and tonoclonic attacks and partial epileptic attacks such as temporal lobe, and complex partial attacks, and furthermore for the treatment and prophylaxis of cardiac damage following myocardial ischemias and damage to the kidneys following renal ischemias, for example acute renal insufficiency, acute renal failure, damage which is caused by drug therapy such as, for example, during ciclosporin therapy or damage which occurs during or after a kidney transplantation. Furthermore, the compounds of the formula I can be used for the treatment of acute myocardial infarction and damage which occurs during and after its lysis under treatment with drugs (for example with TPA, reteplase or streptokinase or mechanically with a laser or Rotablator) and of microinfarcts such as, for example, during and after replacement of the heart valve, aneurysm resections and heart transplantations. The present benzimidazoles I can also be used for the treatment of a revascularization of critically narrowed coronary arteries, for example in PCTA and bypass operations, and critically narrowed peripheral arteries, for example arteries of the leg. Moreover, the benzimidazoles I may be useful in the chemotherapy of tumors and their metastasis and for the treatment of inflammations and rheumatic disorders, for example rheumatoid arthritis. In addition, the compounds of the formula I can be used to treat diabetes mellitus or to treat sepsis and multiorgan failure such as, for example, during septic shock and adult respiratory distress syndrome (ARDS, shock lung).

The novel drug formulations contain a therapeutically effective amount of the compounds I in addition to the conventional drug excipients.

For local external application, for example in the form of powders, ointments or sprays, the active compounds may be present in the conventional concentrations. As a rule, the active compounds are present in an amount of from 0.001 to 1, preferably from 0.001 to 0.1, % by weight.

In the case of internal use, the preparations are administered in single doses. From 0.1 to 100 mg per kg of body weight are administered in a single dose. The formulation can be administered daily in one or more doses, depending on the type and severity of the disorders.

Depending on the desired method of application, the novel drug formulations contain the conventional carriers and diluents in addition to the active compound. For local external application, pharmaceutical excipients such as ethanol, isopropanol, oxethylated castor oil, oxethylated hydrogenated castor oil, polyacrylic acid, polyethylene glycol, polyethylene glycol stearate, ethoxylated fatty alcohols, liquid paraffin, vaseline and lanolin, may be used. For internal use, for example, lactose, propylene glycol, ethanol, starch, talc and polyvinylpyrrolidone are suitable.

Antioxidants, such as tocopherol and butylated hydroxyanisole, and butylated hydroxytoluene, flavor-improving additives, stabilizers, emulsifiers and lubricants may furthermore be present.

The substances contained in the formulation in addition to the active compound, and the substances used in the preparation of pharmaceutical formulations, are toxicologically safe and are compatible with the respective active compound. The preparation of the drug formulations is carried out in a conventional manner, for example by mixing the active compound with other conventional carriers and diluents.

The drug formulations can be administered by various methods of application, for example perorally, parenterally, such as intravenously by infusion, subcutaneously, intraperitoneally and topically. Thus, the formulations such as tablets, emulsions, infusion and injection solutions, pastes, ointments, gels, creams, lotions, powders and sprays are possible.

In addition to the substances stated in the examples, the following compounds are particularly preferred and can be synthesized according to said preparation methods:

1. 2-(N-(O-tert-butoxycarbonyl)piperidin-4-yl) benzimidazole-4-carboxamide
2. 2-(N-methylpiperidin-4-yl)benzimidazole-4-carboxamide
3. 2-(N-isopropylpiperidin-4-yl)benzimidazole-4-carboxamide
4. 2-(N-cyclohexylpiperidin-4-yl)benzimidazole-4-carboxamide
5. 2-(N-trans-4-propylcyclohex-1-yl)piperidin-4-yl) benzimidazole-4-carboxamide
6. 2-(N-benzylpiperidin-4-yl)benzimidazole-4-carboxamide
7. 2-(N-(2-phenyl)eth-1-yl)piperidin-4-yl)benzimidazole-4-carboxamide
8. 2-(N-(2(4-fluorophenyl)eth-1-yl)piperidin-4-yl) benzimidazole-4-carboxamide
9. 2-(N-(2(4-chlorophenyl)eth-1-yl)piperidin-4-yl) benzimidazole-4-carboxamide
10. 2-(N-(2(4-bromophenyl)eth-1-yl)piperidin-4-yl) benzimidazole-4-carboxamide
11. 2-(N-(2(4-iodophenyl)eth-1-yl)piperidin-4-yl) benzimidazole-4-carboxamide
12. 2-(N-(2(4-nitrophenyl)eth-1-yl)piperidin-4-yl) benzimidazole-4-carboxamide
13. 2-(N-(2(4-cyanophenyl)eth-1-yl)piperidin-4-yl) benzimidazole-4-carboxamide
14. 2-(N-(2(4-(trifluoromethyl)phenyl)eth-1-yl)piperidin-4-yl)benzimidazole-4-carboxamide
15. 2-(N-(2(4-methylphenyl)eth-1-yl)piperidin-4-yl) benzimidazole-4-carboxamide
16. 2-(N-(2(4-hydroxyphenyl)eth-1-yl)piperidin-4-yl) benzimidazole-4-carboxamide
17. 2-(N-(2(4-methoxyphenyl)eth-1-yl)piperidin-4-yl) benzimidazole-4-carboxamide 18. 2-(N-(2(4-(N',N'-dimethylamino)phenyl)eth-1-yl) piperidin-4-yl)benzimidazole-4-carboxamide
19. 2-(N-(2(4-(N'-acetylamino)phenyl)eth-1-yl)piperidin-4-yl)benzimidazole-4-carboxamide
20. 2-(N-(2(4-(N'-phenylsulfonylamino)phenyl)eth-1-yl) piperidin-4-yl)benzimidazole-4-carboxamide
21. 2-(N-(2(4-(phenylsulfonyl)phenyl)eth-1-yl)piperidin-4-yl)benzimidazole-4-carboxamide
22. 2-(N-(2(4-(methoxycarbonyl)phenyl)eth-1-yl)piperidin-4-yl)benzimidazole-4-carboxamide
23. 2-(N-acetylpiperidin-3-yl)benzimidazole-4-carboxamide
24. 2-(N-propylpiperidin-3-yl)benzimidazole-4-carboxamide
25. 2-(N-isopropylpiperidin-3-yl)benzimidazole-4-carboxamide
26. 2-(N-cyclohexylpiperidin-3-yl)benzimidazole-4-carboxamide
27. 2-(N-(trans-4-propylcyclohex-1-yl)piperidin-3-yl) benzimidazole-4-carboxamide
28. 2-(N-(2-phenyl)eth-1-yl)piperidin-3-yl)benzimidazole-4-carboxamide
29. 2-(N-(2(4-chlorophenyl)eth-1-yl)piperidin-3-yl) benzimidazole-4-carboxamide
30. 2-pyrrolidin-3-ylbenzimidazole-4-carboxamide
31. 2-(N-acetylpyrrolidin-3-yl)benzimidazole-4-carboxamide
32. 2-(N(O-tert-butoxycarbonyl)pyrrolidin-3-yl) benzimidazole-4-carboxamide
33. 2-(N-propylpyrrolidin-3-yl)benzimidazole-4-carboxamide
34. 2-(N-isopropylpyrrolidin-3-yl)benzimidazole-4-carboxamide
35. 2-(N-cyclohexylpyrrolidin-3-yl)benzimidazole-4-carboxamide
36. 2-(N-(trans-4-propylcyclohex-1-yl)pyrrolidin-3-yl) benzimidazole-4-carboxamide
37. 2-(N-benzylpyrrolidin-3-yl)benzimidazole-4-carboxamide
38. 2-(N-(2-phenyl)eth-1-yl)pyrrolidin-3-yl)benzimidazole-4-carboxamide
39. 2-(N-(2(4-chlorophenyl)eth-1-yl)pyrrolidin-3-yl) benzimidazole-4-carboxamide
40. 2-(N-(2(4-nitrophenyl)eth-1-yl)pyrrolidin-3-yl) benzimidazole-4-carboxamide
41. 2-(N-(2(4-cyanophenyl)eth-1-yl)pyrrolidin-3-yl) benzimidazole-4-carboxamide
42. 2-(N-(2(4-(trifluoromethyl)phenyl)eth-1-yl)pyrrolidin-3-yl)benzimidazole-4-carboxamide
43. 2-(N-(2(4-methylphenyl)eth-1-yl)pyrrolidin-3-yl) benzimidazole-4-carboxamide
44. 2-(N-(2(4-hydroxyphenyl)eth-1-yl)pyrrolidin-3-yl) benzimidazole-4-carboxamide
45. 2-(N-(2(4-methoxyphenyl)eth-1-yl)pyrrolidin-3-yl) benzimidazole-4-carboxamide
46. 2-(N-(2(4-(N',N'-dimethylamino)phenyl)eth-1-yl) pyrrolidin-3-yl)benzimidazole-4-carboxamide
47. 2-(N-(2(4-(N'-acetylamino)phenyl)eth-1-yl)pyrrolidin-3-yl)benzimidazole-4-carboxamide
48. 2-(N-(2(4-(N'-phenylsulfonylamino)phenyl)eth-1-yl) pyrrolidin-3-yl)benzimidazole-4-carboxamide
49. 2-(N-(2(4-phenylsulfonyl)phenyl)eth-1-yl)pyrrolidin-3-yl)benzimidazole-4-carboxamide
50. 2-(N-(2(4-(methoxycarbonyl)phenyl)eth-1-yl) pyrrolidin-3-yl)benzimidazole-4-carboxamide
51. 2-pyrrolidin-3-ylbenzimidazole-4-carboxamide
52. 2-(N-acetylpiperazin-4-yl)benzimidazole-4-carboxamide
53. 2-(N(O-tert-butoxycarbonyl)piperazin-4-yl) benzimidazole-4-carboxamide
54. 2-(N-methylpiperazin-4-yl)benzimidazole-4-carboxamide
55. 2-(N-propylpiperazin-4-yl)benzimidazole-4-carboxamide
56. 2-(N-isopropylpiperazin-4-yl)benzimidazole-4-carboxamide
57. 2-(N-cyclohexylpiperazin-4-yl)benzimidazole-4-carboxamide
58. 2-(N-(trans-4-propylcyclohex-1-yl)piperazin-4-yl) benzimidazole-4-carboxamide
59. 2-(N-benzylpiperazin-4-yl)benzimidazole-4-carboxamide
60. 2-(N-(2-phenyl)eth-1-yl)piperazin-4-yl)benzimidazole-4-carboxamide
61. 2-(N-(2(4-fluorophenyl)eth-1-yl)piperazin-4-yl) benzimidazole-4-carboxamide
62. 2-(N-(2(4-chlorophenyl)eth-1-yl)piperazin-4-yl) benzimidazole-4-carboxamide
63. 2-(N-(2(4-bromophenyl)eth-1-yl)piperazin-4-yl) benzimidazole-4-carboxamide
64. 2-(N-(2(4-iodophenyl)eth-1-yl)piperazin-4-yl) benzimidazole-4-carboxamide
65. 2-(N-(2(4-nitrophenyl)eth-1-yl)piperazin-4-yl) benzimidazole-4-carboxamide
66. 2-(N-(2(4-cyanophenyl)eth-1-yl)piperazin-4-yl) benzimidazole-4-carboxamide
67. 2-(N-(2(4-(trifluoromethyl)phenyl)eth-1-yl)piperazin-4-yl)benzimidazole-4-carboxamide
68. 2-(N-(2(4-methylphenyl)eth-1-yl)piperazin-4-yl) benzimidazole-4-carboxamide
69. 2-(N-(2(4-hydroxyphenyl)eth-1-yl)piperazin-4-yl) benzimidazole-4-carboxamide
70. 2-(N-(2(4-methoxyphenyl)eth-1-yl)piperazin-4-yl) benzimidazole-4-carboxamide
71. 2-(N-(2(4-(N',N'-dimethylamino)phenyl)eth-1-yl) piperazin-4-yl)benzimidazole-4-carboxamide
72. 2-(N-(2(4-(N'-acetylamino)phenyl)eth-1-yl)piperazin-4-yl)benzimidazole-4-carboxamide
73. 2-(N-(2(4-(N'-phenylsulfonylamino)phenyl)eth-1-yl) piperazin-4-yl)benzimidazole-4-carboxamide
74. 2-(N-(2(4-phenylsulfonyl)phenyl)eth-1-yl)piperazin-4-yl)benzimidazole-4-carboxamide
75. 2-(N-(2(4-(methoxycarbonyl)phenyl)eth-1-yl)piperazin-4-yl)benzimidazole-4-carboxamide
76. 2-homopiperazin-4-ylbenzimidazole-4-carboxamide
77. 2-(N-acetylhomopiperazin-4-yl)benzimidazole-4-carboxamide
78. 2-(N(O-tert-butoxycarbonyl)homopiperazin-4-yl) benzimidazole-4-carboxamide
79. 2-(N-methylhomopiperazin-4-yl)benzimidazole-4-carboxamide
80. 2-(N-propylhomopiperazin-4-yl)benzimidazole-4-carboxamide
81. 2-(N-isopropylhomopiperazin-4-yl)benzimidazole-4-carboxamide
82. 2-(N-cyclohexylhomopiperazin-4-yl)benzimidazole-4-carboxamide
83. 2-(N-(trans-4-propylcyclohex-1-yl)homopiperazin-4-yl) benzimidazole-4-carboxamide
84. 2-(N-benzylhomopiperazin-4-yl)benzimidazole-4-carboxamide
85. 2-(N-(2-phenyl)eth-1-yl)homopiperazin-4-yl) benzimidazole-4-carboxamide
86. 2-(N-(2(4-fluorophenyl)eth-1-yl)homopiperazin-4-yl) benzimidazole-4-carboxamide 87. 2-(N-(2(4-chlorophenyl)eth-1-yl)homopiperazin-4-yl) benzimidazole-4-carboxamide
88. 2-(N-(2(4-bromophenyl)eth-1-yl)homopiperazin-4-yl) benzimidazole-4-carboxamide
89. 2-(N-(2(4-iodophenyl)eth-1-yl)homopiperazin-4-yl) benzimidazole-4-carboxamide
90. 2-(N-(2(4-nitrophenyl)eth-1-yl)homopiperazin-4-yl) benzimidazole-4-carboxamide
91. 2-(N-(2(4-cyanophenyl)eth-1-yl)homopiperazin-4-yl) benzimidazole-4-carboxamide
92. 2-(N-(2(4-(trifluoromethyl)phenyl)eth-1-yl) homopiperazin-4-yl)benzimidazole-4-carboxamide
93. 2-(N-(2(4-methylphenyl)eth-1-yl)homopiperazin-4-yl) benzimidazole-4-carboxamide
94. 2-(N-(2(4-hydroxyphenyl)eth-1-yl)homopiperazin-4-yl) benzimidazole-4-carboxamide
95. 2-(N-(2(4-methoxyphenyl)eth-1-yl)homopiperazin-4-yl) benzimidazole-4-carboxamide
96. 2-(N-(2(4-(N',N'-dimethylamino)phenyl)eth-1-yl) homopiperazin-4-yl)benzimidazole-4-carboxamide
97. 2-(N-(2(4-(N'-acetylamino)phenyl)eth-1-yl) homopiperazin-4-yl)benzimidazole-4-carboxamide
98. 2-(N-(2(4-(N'-phenylsulfonylamino)phenyl)eth-1-yl) homopiperazin-4-yl)benzimidazole-4-carboxamide
99. 2-(N-(2(4-phenylsulfonyl)phenyl)eth-1-yl) homopiperazin-4-yl)benzimidazole-4-carboxamide
100. 2-(N-(2(4-(methoxycarbonyl)phenyl)eth-1-yl) homopiperazin-4-yl)benzimidazole-4-carboxamide
101. 1-methyl-2-(piperidin-4-yl)benzimidazole-4-carboxamide
102. 2-(N(O-tert-butoxycarbonyl)piperidin-4-yl)-1-methylbenzimidazole-4-carboxamide
103. 1-methyl-2-(N-methyl-piperidin-4-yl)benzimidazole-4-carboxamide
104. 1-methyl-2-(N-isopropyl-piperidin-4-yl) benzimidazole-4-carboxamide
105. 2-(N-benzylpiperidin-4-yl)-1-methylbenzimidazole-4-carboxamide
106. 1-methyl-2-(N-(2-phenyl)eth-1-yl)piperidin-4-yl) benzimidazole-4-carboxamide
107. 2-(N-(2(4-chlorophenyl)eth-1-yl)piperidin-4-yl)-1-methyl-benzimidazole-4-carboxamide
108. 2-(N-acetylpiperidin-3-yl)-1-methylbenzimidazole-4-carboxamide
109. 1-methyl-2-(pyrrolidin-3-yl)benzimidazole-4-carboxamide
110. 2-(N-acetylpyrrolidin-3-yl)-1-methylbenzimidazole-4-carboxamide
111. 2-(N(O-tert-butoxycarbonyl)pyrrolidin-3-yl)-1-methyl-benzimidazole-4-carboxamide
112. 1-methyl-2-(N-methylpyrrolidin-3-yl)benzimidazole-4-carboxamide
113. 1-methyl-2-(N-propylpyrrolidin-3-yl)benzimidazole-4-carboxamide
114. 1-methyl-2-(N-isopropylpyrrolidin-3-yl) benzimidazole-4-carboxamide
115. 2-(N-benzylpyrrolidin-3-yl)-1-methylbenzimidazole-4-carboxamide
116. 1-methyl-2-(N-(2-phenyl)eth-1-yl)pyrrolidin-3-yl) benzimidazole-4-carboxamide
117. 2-(N-(2(4-chlorophenyl)eth-1-yl)pyrrolidin-3-yl)-1-methylbenzimidazole-4-carboxamide
118. 1-methyl-2-(pyrrolidin-2-yl)benzimidazole-4-carboxamide
119. 2-(N-acetylpyrrolidin-2-yl)-1-methylbenzimidazole-4-carboxamide
120. 1-methyl-2-piperazin-4-ylbenzimidazole-4-carboxamide
121. 2-(N-acetylpiperazin-4-yl)-1-methylbenzimidazole-4-carboxamide
122. 2-(N(O-tert-butoxycarbonyl)piperazin-4-yl)-1-methylbenzimidazole-4-carboxamide
123. 1-methyl-2-(N-methylpiperazin-4-yl)benzimidazole-4-carboxamide
124. 1-methyl-2-(N-propylpiperazin-4-yl)benzimidazole-4-carboxamide
125. 1-methyl-2-(N-isopropylpiperazin-4-yl) benzimidazole-4-carboxamide
126. 2-(N-benzylpiperazin-4-yl)-1-methylbenzimidazole-4-carboxamide
127. 1-methyl-2-(N-(2-phenyl)eth-1-yl)piperazin-4-yl) benzimidazole-4-carboxamide
128. 2-(N-(2(4-chlorophenyl)eth-1-yl)piperazin-4-yl)-1-methyl-benzimidazole-4-carboxamide
129. 2-(homopiperazin-4-yl)-1-metylbenzimidazole-4-carboxamide
130. 2-(N-acetylhomopiperazin-4-yl)-1-methylbenzimidazole-4-carboxamide
131. 2-(N(O-tert-butoxycarbonyl)homopiperazin-4-yl)-1-methyl-benzimidazole-4-carboxamide
132. 1-methyl-2-(N-methylhomopiperazin-4-yl) benzimidazole-4-carboxamide
133. 1-methyl-2-(N-propylhomopiperazin-4-yl) benzimidazole-4-carboxamide
134. 1-methyl-2-(N-isopropylhomopiperazin-4-yl) benzimidazole-4-carboxamide
135. 2-(N-benzylhomopiperazin-4-yl)-1-methylbenzimidazole-4-carboxamide
136. 1-methyl-2-(N-(2-phenyl)eth-1-yl)homopiperazin-4-yl)benzimidazole-4-carboxamide
137. 2-(N-(2(4-chlorophenyl)eth-1-yl)homopiperazin-4-yl)-1-methyl-benzimidazole-4-carboxamide
138. 1-ethyl-2-(piperidin-4-yl)benzimidazole-4-carboxamide
139. 2-(piperidin-4-yl)-1-isopropylbenzimidazole-4-carboxamide
140. 1-(2-(hydroxy)eth-1-yl)-2-(piperidin-4-yl) benzimidazole-4-carboxamide
141. 1-(2-(methoxy)eth-1-yl)-2-(piperidin-4-yl) benzimidazole-4-carboxamide
142. 1-(2-(amino)eth-1-yl)-2-(piperidin-4-yl) benzimidazole-4-carboxamide
143. 1-(2-(N,N-dimethylamino)eth-1-yl)-2-(piperidin-4-yl) benzimidazole-4-carboxamide
144. 1-(2-(piperidin-1-yl)eth-1-yl)-2-(piperidin-4-yl) benzimidazole-4-carboxamide
145. 2-(piperidin-4-yl)-1-(2-(pyrrolidin-1-yl)eth-1-yl) benzimidazole-4-carboxamide
146. 1-(2-(2-ethylpiperidin-1-yl)eth-1-yl)-2-(piperidin-4-yl) benzimidazole-4-carboxamide
147. 1-ethyl-2-(piperidin-3-yl)benzimidazole-4-carboxamide
148. 2-(piperidin-3-yl)-1-isopropylbenzimidazole-4-carboxamide
149. 1-(2-(hydroxy)eth-1-yl)-2-(piperidin-3-yl) benzimidazole-4-carboxamide
150. 1-(2-(methoxy)eth-1-yl)-2-(piperidin-3-yl) benzimidazole-4-carboxamide
151. 1-(2-(amino)eth-1-yl)-2-(piperidin-3-yl) benzimidazole-4-carboxamide
152. 1-(2-(N,N-dimethylamino)eth-1-yl)-2-(piperidin-3-yl) benzimidazol-4-carboxamide
153. 1-(2-(piperidin-1-yl)eth-1-yl)-2-(piperidin-3-yl) benzimidazole-4-carboxamide
154. 2-(piperidin-3-yl)-1-(2-(pyrrolidin-1-yl)eth-1-yl) benzimidazole-4-carboxamide 155. 1-(2-(2-ethyl-piperidin-1-yl)eth-1-yl)-2-(piperidin-3-yl)benzimidazole-4-carboxamide
156. 1-ethyl-2-(pyrrolidin-3-yl)benzimidazole-4-carboxamide
157. 1-isopropyl-2-(pyrrolidin-3-yl)benzimidazole-4-carboxamide
158. 1-(2-(hydroxy)eth-1-yl)-2-(pyrrolidin-3-yl) benzimidazole-4-carboxamide
159. 1-(2-(methoxy)eth-1-yl)-2-(pyrrolidin-3-yl) benzimidazole-4-carboxamide
160. 1-(2-(amino)eth-1-yl)-2-(pyrrolidin-3-yl) benzimidazole-4-carboxamide
161. 1-(2-(N,N-dimethylamino)eth-1-yl)-2-(pyrrolidin-3-yl) benzimidazole-4-carboxamide
162. 1-(2-(piperidin-1-yl)eth-1-yl)-2-(pyrrolidin-3-yl) benzimidazole-4-carboxamide
163. 2-(pyrrolidin-3-yl)-1-(2-(pyrrolidin-1-yl)eth-1-yl) benzimidazole-4-carboxamide
164. 1-(2-(2-ethylpiperidin-1-yl)eth-1-yl)-2-(piperidin-3-yl) benzimidazole-4-carboxamide
165. 1-ethyl-2-(pyrrolidin-2-yl)benzimidazole-4-carboxamide
166. 1-isopropyl-2-(pyrrolidin-2-yl)benzimidazole-4-carboxamide
167. 1-(2-(hydroxy)eth-1-yl)-2-(pyrrolidin-2-yl) benzimidazole-4-carboxamide
168. 1-(2-(methoxy)eth-1-yl)-2-(pyrrolidin-2-yl) benzimidazole-4-carboxamide
169. 1-(2-(amino)eth-1-yl)-2-(pyrrolidin-2-yl) benzimidazole-4-carboxamide
170. 1-(2-(N,N-dimethylamino)eth-1-yl)-2-(pyrrolidin-2-yl) benzimidazole-4-carboxamide
171. 1-(2-(piperidin-1-yl)eth-1-yl)-2-(pyrrolidin-2-yl) benzimidazole-4-carboxamide
172. 2-(pyrrolidin-2-yl)-1-(2-(pyrrolidin-1-yl)eth-1-yl) benzimidazole-4-carboxamide
173. 1-(2-(2-ethyl-piperidin-1-yl)eth-1-yl)-2-(piperidin-2-yl)benzimidazole-4-carboxamide
174. 1-ethyl-2-(piperazin-4-yl)benzimidazole-4-carboxamide
175. 1-isopropyl-2-(piperazin-4-yl)benzimidazole-4-carboxamide
176. 1-(2-(hydroxy)eth-1-yl)-2-(piperazin-4-yl) benzimidazole-4-carboxamide
177. 1-(2-(methoxy)eth-1-yl)-2-(piperazin-4-yl) benzimidazole-4-carboxamide
178. 1-(2-(amino)eth-1-yl)-2-(piperazin-4-yl) benzimidazole-4-carboxamide
179. 1-(2-(N,N-dimethylamino)eth-1-yl)-2-(piperazin-4-yl) benzimidazole-4-carboxamide
180. 2-(piperazin-4-yl)-1-(2-(piperidin-1-yl)eth-1-yl) benzimidazole-4-carboxamide
181. 2-(piperazin-4-yl)-1-(2-(pyrrolidin-1-yl)eth-1-yl) benzimidazole-4-carboxamide
182. 1-(2-(2-ethyl-piperidin-1-yl)eth-1-yl)-2-(piperidin-4-yl)benzimidazole-4-carboxamide
183. 1-ethyl-2-(homopiperazin-4-yl)benzimidazole-4-carboxamide
184. 1-isopropyl-2-(homopiperazin-4-yl)benzimidazole-4-carboxamide
185. 1-(2-(hydroxy)eth-1-yl)-2-(homopiperazin-4-yl) benzimidazole-4-carboxamide
186. 1-(2-(methoxy)eth-1-yl)-2-(homopiperazin-4-yl) benzimidazole-4-carboxamide
187. 1-(2-(amino)eth-1-yl)-2-(homopiperazin-4-yl) benzimidazole-4-carboxamide
188. 1-(2-(N,N-dimethylamino)eth-1-yl)-2-(homopiperazin-4-yl)benzimidazole-4-carboxamide
189. 2-(homopiperazin-4-yl)-1-(2-(piperidin-1-yl)eth-1-yl) benzimidazole-4-carboxamide
190. 2-(homopiperazin-4-yl)-1-(2-(pyrrolidin-1-yl)eth-1-yl) benzimidazole-4-carboxamide
191. 1-(2-(2-ethylpiperidin-1-yl)eth-1-yl)-2-(piperidin-2 (homopiperazin-4-yl)benzimidazole-4-carboxamide
192. 1-ethyl-2-(N-propylpiperidin-4-yl)benzimidazole-4-carboxamide
193. 1-isopropyl-2-(N-propylpiperidin-4-yl)benzimidazole-4-carboxamide
194. 1-(2-(hydroxy)eth-1-yl)-2-(N-propylpiperidin-4-yl) benzimidazole-4-carboxamide
195. 1-(2-(methoxy)eth-1-yl)-2-(N-propylpiperidin-4-yl) benzimidazole-4-carboxamide
b 196. 1-(2-(amino)eth-1-yl)-2-(N-propylpiperidin-4-yl) benzimidazole-4-carboxamide
197. 1-(2-(N,N-dimethylamino)eth-1-yl)-2-(N-propylpiperidin-4-yl)benzimidazole-4-carboxamide
198. 1-(2-(piperidin-1-yl)eth-1-yl)-2-(N-propylpiperidin-4-yl)benzimidazole-4-carboxamide
199. 2-(N-propylpiperidin-4-yl)-1-(2-pyrrolidin-1-yl)eth-1-yl)benzimidazole-4-carboxamide
200. 1-(2-(2-ethylpiperidin-1-yl)eth-1-yl)-2-(N-propylpiperidin-4-yl)benzimidazole-4-carboxamide
201. 1-ethyl-2-(N-propylpiperidin-3-yl)benzimidazole-4-carboxamide
202. 1-isopropyl-2-(N-propylpiperidin-3-yl)benzimidazole-4-carboxamide
203. 1-(2-(hydroxy)eth-1-yl)-2-(N-propylpiperidin-3-yl) benzimidazole-4-carboxamide
204. 1-(2-(methoxy)eth-1-yl)-2-(N-propylpiperidin-3-yl) benzimidazole-4-carboxamide
205. 1-(2-(amino)eth-1-yl)-2-(N-propylpiperidin-3-yl) benzimidazole-4-carboxamide
206. 1-(2-(N,N-dimethylamino)eth-1-yl)-2-(N-propylpiperidin-3-yl)benzimidazole-4-carboxamide
207. 1-(2-(piperidin-1-yl)eth-1-yl)-2-(N-propylpiperidin-3-yl)benzimidazole-4-carboxamide
208. 2-(N-propylpiperidin-3-yl)-1-(2-pyrrolidin-1-yl)eth-1-yl)benzimidazole-4-carboxamide
209. 1-(2-(2-ethylpiperidin-1-yl)eth-1-yl)-2-(N-propylpiperidin-3-yl)benzimidazole-4-carboxamide
210. 1-ethyl-2-(N-propylpyrrolidin-3-yl)benzimidazole-4-carboxamide
211. 1-isopropyl-2-(N-propylpyrrolidin-3-yl) benzimidazole-4-carboxamide
212. 1-(2-(hydroxy)eth-1-yl)-2-(N-propylpyrrolidin-3-yl) benzimidazole-4-carboxamide
213. 1-(2-(methoxy)eth-1-yl)-2-(N-propylpyrrolidin-3-yl) benzimidazole-4-carboxamide
214. 1-(2-(amino)eth-1-yl)-2-(N-propylpyrrolidin-3-yl) benzimidazole-4-carboxamide
215. 1-(2-(N,N-dimethylamino)eth-1-yl)-2-(N-propylpyrrolidin-3-yl)benzimidazole-4-carboxamide
216. 1-(2-(piperidin-1-yl)eth-1-yl)-2-(N-propylpyrrolidin-3-yl)benzimidazole-4-carboxamide
217. 2-(N-propylpyrrolidin-3-yl)-1-(2-pyrrolidin-1-yl)eth-1-yl)benzimidazole-4-carboxamide
218. 1-(2-(2-ethylpiperidin-1-yl)eth-1-yl)-2-(N-propylpyrrolidin-3-yl)benzimidazole-4-carboxamide
219. 1-ethyl-2-(N-propylpyrrolidin-2-yl)benzimidazole-4-carboxamide
220. 1-isopropyl-2-(N-propyl-pyrrolidin-2-yl) benzimidazole-4-carboxamide
221. 1-(2-(hydroxy)eth-1-yl)-2-(N-propylpyrrolidin-2-yl) benzimidazole-4-carboxamide
222. 1-(2-(methoxy)eth-1-yl)-2-(N-propylpyrrolidin-2-yl) benzimidazole-4-carboxamide 223. 1-(2-(amino)eth-1-yl)-2-(N-propylpyrrolidin-2-yl) benzimidazole-4-carboxamide
224. 1-(2-(N,N-dimethylamino)eth-1-yl)-2-(N-propylpyrrolidin-2-yl)benzimidazole-4-carboxamide
225. 1-(2-(piperidin-1-yl)eth-1-yl)-2-(N-propylpyrrolidin-2-yl)benzimidazole-4-carboxamide
226. 2-(N-propylpyrrolidin-2-yl)-1-(2-propylpyrrolidin-1-yl)eth-1-yl)benzimidazole-4-carboxamide
227. 1-(2-(2-ethylpiperidin-1-yl)eth-1-yl)-2-(N-propylpiperidin-2-yl)benzimidazole-4-carboxamide
228. 1-ethyl-2-(N-propylpyrrolidin-4-yl)benzimidazole-4-carboxamide
229. 1-isopropyl-2-(N-propylpiperazin-4-yl)benzimidazole-4-carboxamide
230. 1-(2-(hydroxy)eth-1-yl)-2-(N-propylpiperazin-4-yl) benzimidazole-4-carboxamide
231. 1-(2-(methoxy)eth-1-yl)-2-(N-propylpiperazin-4-yl) benzimidazole-4-carboxamide
232. 1-(2-(amino)eth-1-yl)-2-(N-propylpiperazin-4-yl) benzimidazole-4-carboxamide
233. 1-(2-(N,N-dimethylamino)eth-1-yl)-2-(N-propylpiperazin-4-yl)benzimidazole-4-carboxamide
234. 1-(2-(piperidin-1-yl)eth-1-yl)-2-(N-propylpiperazin-4-yl)benzimidazole-4-carboxamide
235. 2-(N-propyl-piperazin-4-yl)-1-(2-pyrrolidin-1-yl)eth-1-yl)benzimidazole-4-carboxamide
236. 1-(2-(2-ethylpiperidin-1-yl)eth-1-yl)-2-(N-propyl-piperidin-4-yl)benzimidazole-4-carboxamide
237. 1-ethyl-2-(N-propylhomopiperazin-4-yl) benzimidazole-4-carboxamide
238. 1-isopropyl-2-(N-propylhomopiperazin-4-yl) benzimidazole-4-carboxamide
239. 1-(2-(hydroxy)eth-1-yl)-2-(N-propylhomopiperazin-4-yl)benzimidazole-4-carboxamide
240. 1-(2-(methoxy)eth-1-yl)-2-(N-propylhomopiperazin-4-yl)benzimidazole-4-carboxamide
241. 1-(2-(amino)eth-1-yl)-2-(N-propylhomopiperazin-4-yl)benzimidazole-4-carboxamide
242. 1-(2-(N,N-dimethylamino)eth-1-yl)-2-(N-propylhomopiperazin-4-yl)benzimidazole-4-carboxamide
243. 1-(2-(piperidin-1-yl)eth-1-yl)-2-(N-propylhomopiperazin-4-yl)benzimidazole-4-carboxamide
244. 2-(N-propylhomopiperazin-4-yl)-1-(2-pyrrolidin-1-yl) eth-1-yl)benzimidazole-4-carboxamide
245. 1-(2-(2-ethylpiperidin-1-yl)eth-1-yl)-2-(N-propylhomopiperazin-4-yl)benzimidazole-4-carboxamide
246. 6-chloro-2-(piperidin-4-yl)benzimidazole-4-carboxamide
247. 6-chloro-2-(piperidin-3-yl)benzimidazole-4-carboxamide
248. 6-chloro-2-(pyrrolidin-3-yl)benzimidazole-4-carboxamide
249. 6-chloro-2-(piperazin-4-yl)benzimidazole-4-carboxamide
250. 6-chloro-2-(homopiperazin-4-yl)benzimidazole-4-carboxamide
251. 6-ethyl-2-(piperidin-4-yl)benzimidazole-4-carboxamide
252. 6-ethyl-2-(piperidin-3-yl)benzimidazole-4-carboxamide
253. 6-ethyl-2-(pyrrolidin-3-yl)benzimidazole-4-carboxamide
254. 6-ethyl-2-(piperazin-4-yl)benzimidazole-4-carboxamide
255. 6-ethyl-2-(homopiperazin-4-yl)benzimidazole-4-carboxamide
256. 6-amino-2-(piperidin-4-yl)benzimidazole-4-carboxamide
257. 6-amino-2-(piperidin-3-yl)benzimidazole-4-carboxamide
258. 6-amino-2-(pyrrolidin-3-yl)benzimidazole-4-carboxamide
259. 6-amino-2-(piperazin-4-yl)benzimidazole-4-carboxamide
260. 6-amino-2-(homopiperazin-4-yl)benzimidazole-4-carboxamide
261. 2-(piperidin-4-yl)-6-(pyrrolidin-1-yl)benzimidazole-4-carboxamide
262. 2-(piperidin-3-yl)-6-(pyrrolidin-1-yl)benzimidazole-4-carboxamide
263. 2-(pyrrolidin-3-yl)-6-(pyrrolidin-1-yl)benzimidazole-4-carboxamide
264. 2-(piperazin-4-yl)-6-(pyrrolidin-1-yl)benzimidazole-4-carboxamide
265. 2-(homopiperazin-4-yl)-6-(pyrrolidin-1-yl) benzimidazole-4-carboxamide
266. 2-(3-methylpiperidin-4-yl)benzimidazole-4-carboxamide
267. 2-(3-cyclohexylpiperidin-4-yl)benzimidazole-4-carboxamide
268. 2-(2-cyclohexylpiperidin-4-yl)benzimidazole-4-carboxamide
269. 2-(3-phenylpiperidin-4-yl)benzimidazole-4-carboxamide
270. 2-(4-phenylpiperidin-4-yl)benzimidazole-4-carboxamide
271. 2-(2-(hydroxycarbonyl)piperidin-4-yl)benzimidazole-4-carboxamide
272. 2-(2-(ethoxycarbonyl)piperidin-4-yl)benzimidazole-4-carboxamide
273. 2-(2-(cyclohexyloxycarbonyl)piperidin-4-yl) benzimidazole-4-carboxamide
274. 2-(2-(benoxycarbonyl)piperidin-4-yl)benzimidazole-4-carboxamide
275. 2-(2-(phenoxycarbonyl)piperidin-4-yl)benzimidazole-4-carboxamide

EXAMPLE 1

2-(Piperidin-4-yl)benzimidazole-4-carboxamide.2 HCl

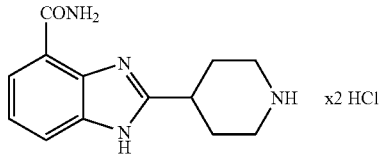

a) N-(2-Amino-3-ethoxycarbonyl)-1-(tert-butoxycarbonyl) piperidine-4-carboxanilide 5.5 g (24 mmol) of 1-(tert-butoxycarbonyl)piperidine-4-carboxylicacid and 4.3 g (24 mmol) of ethyl 2,3-diaminobenzoate were dissolved with 6.0 g (60 mmol) of triethylamine and 3.2 g (24 mmol) of 1-hydroxybenzotriazole in 100 ml of anhydrous tetrahydrofuran. At 0° C., 4.6 g (24 mmol) of N'-(3-dimethylaminopropyl)-N-ethylcarbodiimide were then added and the whole was stirred for 1 hour. Stirring was then continued for 24 hours at room temperature. The reaction mixture was evaporated down under reduced pressure and the residue obtained was partitioned between ethyl acetate and aqueous sodium bicarbonate solution. The ethyl acetate phase was also washed with 5% strength aqueous citricacid solution, dried and evaporated down under reduced pressure. 8.4 g of the product were obtained.

b) Ethyl 2-(1-(tert-butoxycarbonyl)piperidin-4-yl) benzimidazole-4-carboxylate 8.1 g of the intermediate 1a in 100 ml of concentrated acetic acid were refluxed for 30 minutes. The whole was then evaporated down under reduced pressure and the residue was partitioned between ethyl acetate and water. The ethyl acetate phase was also washed with aqueous sodium bicarbonate solution and water then evaporated down under reduced pressure. 4.6 g of the product were obtained.

c) 2-Piperidin-4-ylbenzimidazole-4-carboxylate×2 HCl 3.7 g (9.9 mmol) of the intermediate 1b were added to 50 ml of a 4M solution of hydrogen chloride in dioxane and stirred for 1 hour at room temperature. Thereafter, the batch was diluted with a large amount of ether and the resulting precipitate was filtered off with suction. 3.2 g of the product was obtained.

d) 2-Piperidin-4-ylbenzimidazole-4-carbohydrazide 2.7 g (7.8 mmol) of the intermediate 1c and 2.7 g (54 mmol) of hydrazine in 30 ml of n-butanol were refluxed for 15 hours. Thereafter, the whole was evaporated down under reduced pressure and the residue obtained was partitioned between ethyl acetate and aqueous sodium bicarbonate solution. The organic phase was separated off, dried and evaporated down under reduced pressure. 0.9 g of the product was obtained.

e) 2-Piperidin-4-ylbenzimidazole-4-carboxamide×2 HCl

About 2.4 g of Raney nickel in 20 ml of water were added to 0.8 g (3.1 mmol) of the intermediate 1d in 20 ml of dimethylformamide, and the whole was heated to 100° C. for 8 hours. The reaction mixture was then filtered. The residue was taken up in ethanol and a crude product was precipitated by adding ether. The precipitate was dissolved in isopropanol, and a solution of hydrogen chloride in isopropanol was added. The resulting precipitate was filtered off with suction. 0.52 g of the product was obtained.

$^1$H-NMR ($D_6$-DMSO). δ=1.8–2.3 (4H), 2.8–3.5 (5H), 7.2 (1H), 7.7 (1H), 7.8 (1H), 8.5 (broad) and 9.2 (broad) ppm.

EXAMPLE 2

2-Piperidin-4-ylbenzimidazole-4-carboxamide

The example was prepared analogously to Example 1.

$^1$H-NMR ($D_6$-DMSO). δ=1.7 (1H), 1.9–2.2 (4H), 2.75 (1H), 3.8 (1H), 7.2 (1H), 7.6 (1H), 7.8 (1H) and 9.3 (broad) ppm.

EXAMPLE 3

2-(N-Acetylpiperidin-4-yl)benzimidazole-4-carboxamide a) Methyl 2-(N-acetylpiperidin-4-yl)benzimidazole-4-carboxylate 3.3 g (19.9 mmol) of methyl 2,3-diaminobenzoate were dissolved in 100 ml of methanol, and a solution of 4.0 g (25.8 mmol) of N-acetylpiperidine-4-carbaldehyde in 100 ml of methanol was added dropwise at room temperature. The whole was stirred for about 10 minutes at room temperature. Thereafter, 5.2 g (25.8 mmol) of copper(II) acetate, which was dissolved in 100 ml of water, were added dropwise and the whole was refluxed for 30 minutes. After cooling, 25 ml of concentrated hydrochloricacid were added carefully and the whole was again refluxed. 7.15 g (29.8 mmol) of sodium sulfide nonahydrate, dissolved in 100 ml of water, were then added dropwise and the whole was boiled for a further 10 minutes. After cooling, the reaction solution was evaporated down under reduced pressure. The residue obtained was dispersed in water and filtered. The filtrate was rendered alkaline with aqueous sodium bicarbonate solution and was extracted several times with ethyl acetate. The combined organic phases were washed with water, dried and evaporated down under reduced pressure. 4.5 g of the product were obtained.

b) 2-(N-Acetylpiperidin-4-yl)benzimidazole-4-carbohydrazide 4.3 g (14.9 mmol) of the intermediate 3a were refluxed with 3.7 g (74.3 mmol) of hydrazine hydrate in 100 ml of ethanol for 2.5 hours. The whole was then evaporated down under reduced pressure, the crude product obtained being used directly in the following reaction step.

c) 2-(N-Acetylpiperidin-4-yl)benzimidazole-4-carboxamide 5 g Raney nickel were added to a mixture of 100 ml of dimethylformamide and 50 ml of water. The residue from reaction step 3b, dissolved with water, was then carefully added dropwise at room temperature so that the gas evolution observed could be controlled. The whole was then heated to 100° C. for 2 hours. After cooling, filtration was carried out and the filtrate was evaporated down under reduced pressure. The residue obtained was taken up in a little methylene chloride and the product was precipitated by carefully adding ether. 3.2 g of the product were obtained.

$^1$H-NMR ($D_6$-DMSO). δ=1.8–2.3 (4H), 2.8–3.5 (5H), 7.2 (1H), 7.7 (1H), 7.8 (1H), 8.5 (broad) and 9.2 (broad) ppm.

EXAMPLE 4

2-(N-Propylpiperidin-4-yl)benzimidazole-4-carboxamide 0.25 g (1 mmol) of the product from Example 2, 59 mg (1 mmol) of n-propanal and 125 μl (2 mmol) of acetic acid were dissolved in 25 ml of ethanol. Thereafter, 64 mg (1 mmol) of sodium cyanoborohydride were added at room temperature and the whole was stirred for 16 hours. The reaction solution was evaporated down under reduced pressure and the residue was partitioned between methylene chloride and aqueous sodium bicarbonate solution. The organic phase was washed with water, separated off, dried and evaporated down under reduced pressure. The residue obtained was purified chromatographically using the mobile phase 4/1 ethyl acetate/methanol. 0.07 g of the product being obtained.

$^1$H-NMR ($D_6$-DMSO). δ=0.9 (3H), 1.5 (2H), 1.9 (2H), 2.3 (2H), 2.9 (2H), 3.3 (1H), 7.25 (1H), 7.6 (1H), 7.8 (1H), 9.3 (1H) and 12.8 (1H) ppm.

EXAMPLE 5

2-Piperidin-3-ylbenzimidazole-4-carboxamide×2 HCl 1.3 g (3.8 mmol) of the product from Example 6 were dissolved in 20 ml of isopropanol, and 50 ml of isopropanolic hydrochloride solution were added. The whole was stirred for 1 hour at room temperature. The resulting precipitate was filtered off with suction, 1.1 g of the product being obtained.

$^1$H-NMR ($D_6$-DMSO). δ=1.95–2.3 (3H), 2.45 (1H), 3.2 (1H), 3.5 (1H), 3.9 (1H), 7.6 (1H) and 7.95 (2H) ppm.

EXAMPLE 6

2-(N-(O-tert-Butoxycarbonyl)piperidin-3-yl) benzimidazole-4-carboxamide a) Ethyl 2-amino-3-(N—(O-tert-butoxycarbonyl)piperidin-3-yl)amido-benzoate 4 g (17.4 mmol) of N—(O-tert-butoxycarbonyl) piperidine-3-carboxylicacid and 4.8 ml (34.9 mmol) of triethylamine were dissolved in 100 ml of anhydrous tetrahydrofuran. 1.7 ml (17.4 mmol) of ethyl chloroformate, dissolved in 10 ml of anhydrous tetrahydrofuran, were then added dropwise at −10° C. The whole was stirred for 1 hour at 0° C. Thereafter, 2.9 g (17.4 mmol) of methyl 2,3-diaminobenzoate were added, once again at −10° C., and the whole was stirred for 12 hours at room temperature. The reaction solution was evaporated down under reduced pressure and the residue obtained was partitioned between ethyl acetate and water. The organic phase was also washed with aqueous sodium bicarbonate solution and water, dried and evaporated down under reduced pressure. 5.5 g of the product were obtained.

b) Methyl 2-(N—(O-tert-butoxycarbonyl)piperidin-3-yl) benzimidazole-4-carboxylate 5.4 g (14.3 mmol) of the product from 6a in 100 ml of acetic acid were refluxed for 75 minutes. After cooling, the whole was evaporated down under reduced pressure and the resulting residue was purified chromatographically using the mobile phase 1/1 ethyl acetate/heptane. 2.7 g of the product were obtained.

c) 2-(N—(O-tert-Butoxycarbonyl)piperidin-3-yl benzimidazole-4-carbohydrazide 2.3 g (6.4 mmol) of the product from 6b were refluxed with 1.6 g (32 mmol) of hydrazine hydrate in 20 ml of ethanol for 2.5 hours. After cooling, the whole was evaporated down under reduced pressure. The residue was treated with water, the resulting precipitate being filtered off with suction and dried. 1.6 g of the product were obtained.

d) 2-(N-O-tert-Butoxycarbonyl)piperidin-3-yl) benzimidazole-4-carboxamide 1.6 g of the product from 6c were reacted analogously to the method from 3c. 1.3 g of the product were obtained.

$^1$H-NMR ($D_6$-DMSO). δ=1.4 (1H), 1.5 (1H), 2.9 (1H), 3.1 (1H), 3.9 (1H), 4.2 (1H), 7.3 (1H), 7.7 (1H), 7.8 (1H), 9.1 (broad) and 13 (broad) ppm.

The substances mentioned in the following examples were prepared in analogy to Examples 1 to 6:

EXAMPLE 7

2-(N-Benzylpiperidin-3-yl)benzimidazole-4-carboxamide $^1$H-NMR ($D_6$-DMSO); δ=1.6–1.8(3H), 2.1(2H), 2.3(1H), 2.8(1H), 3.1(1H), 3.2(1H), 3.5(2H), 7.2–7.4(6H), 7.6(2H), 7.8(2H) and 9.2 (broad) ppm.

EXAMPLE 8

2-(N-Methylpiperidin-3-yl)benzimidazole-4-carboxamide×2 HCl $^1$H-NMR ($D_2O$); δ=2.1(2H), 2.3(1H), 2.5(1H), 3.1(3H), 3.2(1H), 3.5(1H), 4.0(2H), 7.7(1H) and 8.0(2H) ppm.

EXAMPLE 9

2-Piperazin-4-yl-benzimidazole-4-carboxamide $^1$H-NMR ($D_6$-DMSO); δ=2.5(4H), 3.3(4H), 7.2(1H), 7.6–7.7(2H), 7.8(1H) and 9.3(1H) ppm.

EXAMPLE 10

2-(N-Propylpiperidin-3-yl)benzimidazole-4-carboxamide×2 HCl $^1$H-NMR ($D_6$-DMSO); δ=0.9(3H), 1.5(2H), 1.9(2H), 2.0 (4H), 2.3(2H), 2.9(3H), 7.2(1H), 7.6(2H), 7.8(1H) and 9.3 (broad) ppm.

EXAMPLE 11

2-(N-(3-Phenylprop-1-yl)-piperidin-3-yl) benzimidazole-4-carboxamide×2HCl $^1$H-NMR ($D_6$-DMSO): δ=2.0–2.5(6H), 2.8(2H), 3.1(1H), 3.2–3.4(3H), 3.7(1H), 3.8–4.0(2H), 7.3–7.5(5H), 7.7(1H) and 8.0(2H) ppm.

EXAMPLE 12

2-(N-Benzoylpiperidin-3-yl)benzimidazole-4-carboxamide $^1$H-NMR ($CF_3COOD$): δ=1.9(1H), 2.6(1H), 3.8(1H), 3.9–4.2(4H), 4.3(1H), 4.8(1H) and 7.5–8.2(8H) ppm.

EXAMPLE 13

2-(N-Benzoylpiperidin-4-yl)benzimidazole-4-carboxamide×2 HCl $^1$H-NMR ($D_2O$): δ=2.3(2H), 2.6(2H), 3.3(2H), 3.8(3H), 4.5(2H) and 7.5–8.0(8H) ppm.

EXAMPLE 14

2-(1-(1-Methylpiperidin-4-yl)piperidin-4-yl) benzimidazole-4-carboxamide×3 HCl $^1$H-NMR ($D_6$-DMSO): δ=1.4(2H), 1.6–2.0(6H), 2.0–2.4 (7H), 2.7–3.0(6H), 7.2(1H), 7.7(2H), 7.8(1H) and 9.4 (broad) ppm.

EXAMPLE 15

2-(N-n-Pentylpiperidin-4-yl)benzimidazole-4-carboxamide $^1$H-NMR ($D_6$-DMSO): δ=0.9(3H), 1.2–1.5(6H), 1.7–2.1 (6H), 2.3(2H), 2.8–3.0(4H), 7.3(1H), 7.6–7.8(3H), 9.4(1H) and 12.8 (broad) ppm.

EXAMPLE 16

2-(N-Isobut-1-yl-piperidin-4-yl)benzimidazole-4-carboxamide $^1$H-NMR ($D_6$DMSO): δ=0.9(6H), 1.8–2.1(10H), 2.9 (2H), 7.2(1H), 7.6(2H), 7.8(1H), 9.2(1H) and 12.5 (broad) ppm.

EXAMPLE 17

2-(N-n-Butylpiperidin-4-yl)benzimidazole-4-carboxamide×HCl $^1$H-NMR ($D_6$-DMSO): δ=0.9(3H), 1.3(2H), 1.7(2H), 2.2–2.4(4H), 3.0–3.2(4H), 3.4–3.6(3H), 7.5(1H), 7.8–8.0 (2H), 8.0(1H), 8.7 (broad) and 10.9 (broad) ppm.

EXAMPLE 18

2-(N-(3-Methyl-but-1-yl)piperidin-4-yl) benzimidazole-4-carboxamide×HCl $^1$H-NMR ($D_6$-DMSO): δ=0.9(6H), 1.7(3H), 2.2–2.4(4H), 3.1(4H), 3.3(1H), 3.7(2H), 7.5(1H), 7.8–8.0(3H), 8.7 (broad) and 10.5 (broad) ppm.

EXAMPLE 19

2-(1,4-Dimethylpiperazin-2-yl)benzimidazole-4-carboxamide×2 HCl $^1$H-NMR ($D_6$-DMSO): δ=2.5 (3H), 2.9 (3H), 3.3–3.8 (5H), 3.9 (1H), 5.0 (1H), 7.4 (1H), 7.7 (1H), 7.8 (1H), 7.9 (1H) and 8.6 (broad) ppm.

EXAMPLE 20

2-Piperazin-2-yl-benzimidazole-4-carboxamide×2 HCl 1.83 g (3.67 mmol) of the product from Example 23 were introduced into 250 ml of methanol with 1 g of 10% palladium on carbon and hydrogenated with about 165 ml of hydrogen. The catalyst was filtered off with suction, and the filtrate was concentrated. The residue was dissolved in 20 ml of isopropanol, and 50 ml of isopropanolic hydrochloricacid solution were added. The resulting precipitate was filtered off with suction to obtain 1.1 g of the product.

$^1$H-NMR ($D_6$-DMSO): δ=3.2–3.7(5H), 4.0(1H), 5.2(1H), 7.4(1H), 7.8(1H), 7.9(1H) and 10.2 (broad) ppm.

EXAMPLE 21

2-(N-Isopropylpiperidin-4-yl)benzimidazole-4-carboxamide×HCl $^1$H-NMR ($D_6$-DMSO): δ=1.25(6H), 2.3(4H), 3. 1(1H), 3.4–3.6(4H), 3.7(1H), 7.5(1H), 7.7–8.0(3H), 8.7(1H) and 10.7 (broad) ppm.

EXAMPLE 22

2-(4-(2-Ethyl-prop-1-yl)piperidin-4-yl) benzimidazole-4-carboxamide

EXAMPLE 23

2-(1,4-Dibenzylpiperazin-2-yl)benzimidazole-4-carboxamide×2 HCl $^1$H-NMR ($D_6$-DMSO): δ=2.95–3.7 (7H), 3.8–4.9 (4H), 7.1–7.55 (8H), 7.65 (2H), 7.85 (2H), 7.94 (1H), 8.7 (broad) and 12.2 (broad) ppm.

EXAMPLE 24

2-(N-Benzylpiperidin-4-yl)-1-(1-benzylpiperidin-4-ylcarbonyl)benzimidazole-4-carboxamide $^1$H-NMR ($D_6$-DMSO): δ=1.7(2H), 1.8–2.0(6H), 2.1(4H), 2.5–2.7(2H), 2.8–3.0(4H), 3.5(4H), 7.2–7.5(11H), 7.7(1H), 8.6(1H), 9.5(1H), 12.3 (broad) ppm.

Exmaple A

Inhibition of the Enzyme poly(ADP-ribose) polymerase or PARP (EC 2.4.2.30)

A 96-well microtiter plate (Falcon) was coated with histones (type II-AS; SIGMA H7755). In addition, histones were dissolved in carbonate buffer (0.05 M $NaHCO_3$; pH 9.4) to a concentration of 50 μg/ml. The individual wells of the microtiter plate were incubated overnight, each with 100 μl of the histone solution. Thereafter, the histone solution was removed and the individual wells were incubated with 200 μl of a 1% strength BSA (bovine serum albumin) solution in carbonate buffer for 2 hours at room temperature. Washing was then carried out three times with wash buffer (0.05% Tween10 in PBS). For the enzyme reaction, 50 μl of the enzyme reaction solution per well (5 μl of reaction buffer (1M Tris-HCl pH 8.0, 100 mM $MgCl_2$, 10 mM DTT), 0.5 μl of PARP (c=0.22 μg/μl), 4 R1 activated DNA (SIGMA D-4522, 1 mg/ml in water), 40.5 μl of $H_2O$ were preincubated with 10 μl of an inhibitor solution for 10 minutes. The enzyme reaction was started by adding 40 μl of a substrate solution (4 μl of reaction buffer (see above), 8 μl of NAD solution (100 μm in $H_2O$), 28 μl of $H_2O$). The reaction time was 20 minutes at room temperature. The reaction was stopped by washing three times with wash buffer (see above). This was followed by incubation for one hour at room temperature with a specific anti-poly-ADP-ribose antibody. The antibodies used were monoclonal anti-poly(ADP-ribose) antibodies "10H" (Biomol SA-276).

The antibodies were used in a 1:5000 dilution in antibody buffer (1% BSA and PBS; 0.05% Tween20). Washing three times with wash buffer was followed by incubation for an hour at room temperature with the secondary antibody. Here, an anti-mouse-IgG coupled with peroxidase (Boehringer Mannheim) was used for the monoclonal antibody and an anti-rabbit-IgG coupled with peroxidase (SIGMA A-6154) was used for the rabbit antibody, each in a 1:10,000 dilution in an antibody buffer. After washing three times with wash buffer, the color reaction was carried out using a 100 μl/well of color reagent (SIGMA, TMB ready-mix, T8540) for about 15 minutes at room temperature. The color reaction was stopped by a 100 μl of 2M $H_2SO_4$. Measurement was then carried out immediately (450 against 620 nm; ELISA "Easy Reader" EAR340AT plate reader, SLT-Lab instruments, Austria). The $K_i$ can be determined in a conventional manner from the inhibition curves at various substrate concentrations.

Example B

Determination of the Water Solubility

A compound to be measured was dissolved directly in a specified volume of water and the resulting solution was brought to a pH of from 5 to 6 with a sodium acetate solution so that the concentration of the active compound to be tested was reached. If the test substance was not present as a water-soluble salt, it was dissolved in a very small amount of dimethyl sulfoxide and then diluted with water (final concentration of dimethyl sulfoxide≦1%), after which the pH was adjusted here too. Here, Example 1 according to the invention gave a solubility of >0.5%.

We claim:

1. The compound of the formula Ia or Ib

Ia

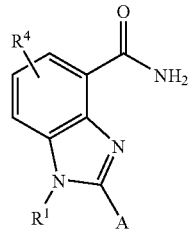

-continued

Ib

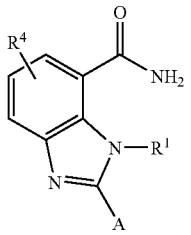

$R^1$ is hydrogen or branched or straight-chain $C_1$–$C_8$-alkyl, where one carbon atom of the alkyl radical [may furthermore carry] *is optionally substituted by* $OR^5$ [(] where $R^5$ is hydrogen or $C_1$–$C_4$-alkyl[)], or one carbon atom in the [chain may also carry] *alkyl radical is optionally substituted by* an =O group $NR^8R^9$, where $R^8$ and $R^9$, independently of one another, are each hydrogen or $C_1$–$C_4$-alkyl or $NR^8R^9$ together [may be] *form* a cyclic amine having 4 to 8 ring atoms, where the carbon chains in $R^8$ or $R^9$ or the ring formed by $NR^8R^9$ [may furthermore carry] *are optionally substituted by* a radical $R^6$ which, independently of $R^2$, [may have] *has* the same meaning as $R^2$, $R^4$ is hydrogen, branched or straight-chain $C_1$–$C_8$-alkyl, chlorine, bromine, fluorine, nitro, cyano, $NR^8R^9$, NH—CO—$R^{10}$ or $OR^8$, where $R^8$ and $R^9$, independently of one another, are each hydrogen or $C_1$–$C_4$-alkyl or $NR^8R^9$ together [may be] *form* a cyclic amine having 4 to 8 ring atoms, where the ring [may furthermore carry] *is optionally substituted by* a radical [(] *selected from the group consisting of* branched or straight-chain $C_1$–$C_6$-alkyl, $C_3$–$C_7$-cycloalkyl-$C_1$–$C_4$-alkyl, CO—$R^{41}$, $COOR^{41}$ [or] *and* phenyl[)], and $R^{10}$ [may be] *is* hydrogen, $C_1$–$C_4$-alkyl or phenyl and $R^{41}$ [may have] *has* the same meanings as $R^{21}$, A is a saturated or monounsaturated heterocyclic, 4- to 8-membered ring which contains one or two nitrogen atoms, and optionally, an oxygen or sulfur atom which ring is substituted by $R^2$ and $R^3$, where $R^2$ is hydrogen[,] *or* branched or straight-chain $C_1$–$C_8$-alkyl which [may furthermore be] *is optionally* substituted by $R^{23}$, and a carbon atom of the chain [may carry] *is optionally substituted by* an =O group, $C_3$–$C_7$-cycloalkyl-$C_1$–$C_4$-alkyl, —CO—$(NH)_{0.1}$[—] $R^{21}$, $COOR^{21}$ or phenyl, where $R^{21}$ is hydrogen, branched or straight-chain $C_1$–$C_6$-alkyl, $C_3$–$C_7$-cycloalkyl-$C_1$–$C_4$-alkyl, phenyl-$C_1$–$C_4$-alkyl, $C_3$–$C_7$-cycloalkyl or phenyl, and each radical [may furthermore carry] *is optionally substituted by* $(CH_2)_{0-2}$—$R^{23}$, and the respective phenyl ring [in turn may furthermore be] *is optionally* substituted by 1, 2 or 3 *of the* following radicals[:] *selected from the group consisting of* chlorine, fluorine, bromine, iodine, branched and straight-chain $C_1$–$C_4$-alkyl, nitro, $CF_3$, cyano, —$(CH_2)_{0-2}$ —$NR^{24}R^{25}$, NH—CO—$R^{10}$, $OR^{10}$, $COOR^{10}$, $SO_2$—$C_1$–$C_4$-alkyl, $SO_2Ph$, $SO_2NH_2$, $NHSO_2$—$C_1$–$C_4$-alkyl, $NHSO_2Ph$ and $CF_3$, where $R^{24}$ and [$R^{26}$]$R^{25}$, independently of one another, are each hydrogen or $C_1$–$C_4$-alkyl or $NR^{24}R^{25}$ together [may be] *are* a [cyclicamine] *cyclic amine* having 4 to 8 ring atoms, where the ring [may furthermore carry] *is optionally substituted by* a radical *selected from the group consisting* of branched or straight-chain $C_1$–$C_8$-alkyl, $C_3$–$C_7$-cycloalkyl-$C_1$–$C_4$-alkyl, CO—$R^{22}$, $COOR^{22}$ [(] where $R^{22}$ is hydrogen, branched or straight-chain $C_1$–$C_6$-alkyl, $C_3$–$C_7$-cycloalkyl-$C_1$–$C_4$-alkyl, phenyl-$C_1$–$C_4$- alkyl, $C_3$–$C_7$-cycloalkyl or phenyl[) or] *and* phenyl, and $R^{10}$ is hydrogen, $C_1$–$C_4$-alkyl or phenyl, and $R^{23}$ is $NR^{26}N^{27}$ where $R^{26}$ and $R^{27}$ are each hydrogen, $C_1$–$C_6$-alkyl, $C_0$–$C_4$-alkylphenyl, where the phenyl ring[may furthermore be] *is optionally* substituted by up to 3 radicals *selected from the group consisting of* Cl, F, Br, I, $C_1$–$C_4$-alkyl, $CF_3$, CN, $SO_2$–$C_1$–$C_4$-alkyl, $SO_2$-phenyl, $NO_2$, $NH_2$, NHCO—$C_1$–$C_4$-alkyl, NHCO-phenyl, OH, O—$C_1$–$C_4$-alkyl, *and* O—$C_1$–$C_4$-alkylphenyl, or $NR^{26}R^{27}$ [may also be] *together are* a [cyclicamine] *cyclic amine* having 3 to 8 members, in which O, N and S as a further hetero atom [may additionally be] *are optionally* present, and the ring [may furthermore be] *is optionally* substituted by a radical $R^{23}$ where $R^{26}$ [may be] *is* $C_1$–$C_4$-alkyl [and] *or* $C_1$–$C_4$-alkylphenyl, $R^3$ is hydrogen, branched or straight-chain $C_1$–$C_6$alkyl[,] *or* $C_3$–$C_7$-cycloalkyl-$C_1$–$C_4$-alkyl which is unsubstituted or substituted by $C_1$–$C_6$-alkyl or $C_3$–$C_7$-cycloalkyl which is unsubstituted or substituted by $C_1$–$C_6$-alkyl, where one carbon atom of the radical [may furthermore carry] *is optionally substituted by* a phenyl ring which [in turn may also be] *is optionally* substituted by 1, 2 or 3 [of the following] radicals[:] *selected from the group consisting of* chlorine, fluorine, bromine, iodine, branched and straight-chain $C_1$–$C_4$-alkyl, nitro, $CF_3$, cyano, $(CH_2)_{0-2}$—$NR^{32}R^{33}$, NH—CO—$R^{10}$, $OR^{10}$, $COOR^{10}$, $SO_2$—$C_1$–$C_4$-alkyl, $SO_2Ph$, $CH_3$, $SO_2NH_2$, $NHSO_2$[-]—$C_1$–$C_4$-alkyl, $NHSO_2Ph$ and $CF_3$, where $R^{32}$ and $R^{33}$, independently of one another, are each hydrogen or $C_1$–$C_4$-alkyl or $NR^{32}R^{33}$ together [may be] *are* a cyclicamine having 4 to 8 ring atoms, where the ring [may furthermore carry] *is optionally substituted by* a radical *selected from the group consisting* of branched or straight-chain $C_1$–$C_6$-alkyl, $C_3$–$C_7$-cycloalkyl-$C_1$–$C_4$-alkyl, CO—$R^{31}$, $COOR^{31}$ [or] *and* phenyl, and $R^{10}$ is hydrogen, $C_1$–$C_4$-alkyl or phenyl, and $R^{31}$ [may have] *has* the same meaning as $R^{21}$, or a tautomeric enantiomeric or diastereomeric form, a prodrug or a physiologically tolerated salt thereof.

2. A compound as claimed in claim 1, wherein $R^1$, $R^2$ and $R^4$ are each hydrogen and A is piperidine, pyrrolidine, piperazine, morpholine and homopiperazine and $R^3$ is bonded to the nitrogen of A.

3. A compound as claimed in claim 1, wherein A [may be piperdine] *is piperidine* which has bonded to the 2-position on the benzimidazole and $R^3$ [may be] *is* hydrogen, $C_1$–$C_4$-alkyl, benzyl or phenyl ethyl and is in the 1-position on the piperidine ring.

4. A composition for treating disorders in which pathologically increased PARP activities occur which comprises an effective amount of a compound as described in claim 1 and a pharmaceutical carrier or excipient.

5. A method of treating patients having disorders in which pathologically increased PARP activities occur comprising administering a therapeutically effective amount of a compound of claim 1 to said patient.

6. The method of claim 5, wherein the disorders are neurodegenerative disorders and neuronal damage.

7. The method of claim 6, wherein the disorders are neurodegenerative disorders and neuronal damage which are caused by ischemia, trauma or massive bleeding.

8. The method of claim 6, wherein the neurodegenerative disorders and neuronal damage are caused by stroke [and] *or* craniocerebral trauma.

9. The method of claim 6, wherein the neurodegenerative disorders and neuronal damage are caused by Alzheimer's disease, Parkinson's disease or Huntington's disease.

10. A method for the treatment or prophylaxis of damage through ischemias comprising administering a therapeutically effective amount of a compound of claim 1 to a patient in need thereof.

11. A method for treating epilepsies comprising administering a therapeutically effective amount of a compound of claim 1 to a patient in need thereof.

12. A method for treating renal damage following renal ischemias, damage which is caused by drug therapy, [and] *or* for treatment during and after kidney transplantations comprising administering a therapeutically effective amount of a compound of claim 1 to a patient in need thereof.

13. A method for treating cardiac damage following myocardial ischemias and damage which is caused by reperfusion of narrowed or closed vessels comprising administering a therapeutically effective amount of a compound of claim 1 to a patient in need thereof.

14. A method for treating microinfarcts comprising administering a therapeutically effective amount of a compound of claim 1 to a patient in need thereof.

15. A method for treatment associated with revascularization of critically narrowed coronary arteries comprising administering a therapeutically effective amount of a compound of claim 1 to a patient in need thereof.

16. A method for treating acute myocardial infarction [and] *or* damage during or after its lysis by means of drugs or mechanically comprising administering a therapeutically effective amount of a compound of claim 1 to a patient in need thereof.

17. A method for treating tumors and their metastasis comprising administering a therapeutically effective amount of a compound of claim 1 to a patient in need thereof.

18. A method for treating sepsis [and] *or* multiorgan failure comprising administering a therapeutically effective amount of a compound of claim 1 to a patient in need thereof.

19. A method for treating immunological disorders comprising administering a therapeutically effective amount of a compound of claim 1 to a patient in need thereof.

20. A method for treating diabetes mellitus comprising administering a therapeutically effective amount of a compound of claim 1 to a patient in need thereof.

*21. A compound as claimed in claim 1 wherein A is piperidine.*

*22. A compound as claimed in claim 1 wherein A is pyrrolidine.*

*23. 2-(N-Propylpiperidin-4-yl)benzimidazole-4-carboxamide.*

*24. 2-(N-Isopropylpiperidine-4-yl)benzimidazole-4-carboxamide HCl.*

*25. A composition for treating disorders in which pathologically increased PARP activities occur which comprises an effective amount of a compound as described in claim 22 and a pharmaceutical carrier or excipient.*

*26. A composition for treating disorders in which pathologically increased PARP activities occur which comprises an effective amount of a compound as described in claim 23 and a pharmaceutical carrier or excipient.*

*27. A composition for treating disorders in which pathologically increased PARP activities occur which comprises an effective amount of a compound as described in claim 24 and a pharmaceutical carrier or excipient.*

*28. A method of treating patients having disorders in which pathologically increased PARP activities occur which comprising administering a therapeutically effective amount of a compound of claim 22 to said patient.*

*29. A method of treating patients having disorders in which pathologically increased PARP activities occur which comprising administering a therapeutically effective amount of a compound of claim 23 to said patient.*

*30. A method of treating patients having disorders in which pathologically increased PARP activities occur which comprising administering a therapeutically effective amount of a compound of claim 24 to said patient.*

*31. A method for treating tumors and their metastasis comprising administering a therapeutically effective amount of a compound of claim 22 to a patient in need thereof.*

*32. A method for treating tumors and their metastasis comprising administering a therapeutically effective amount of a compound of claim 23 to a patient in need thereof.*

*33. A method for treating tumors and their metastasis comprising administering a therapeutically effective amount of a compound of claim 4 to a patient in need thereof.*

*34. A compound of claim 21 wherein the 4 position of the piperidine ring is bound to the 2 position of the benzimidazole ring.*

*35. A compound of claim 34 wherein $R^1$ and $R^4$ are hydrogen.*

*36. A compound of claim 22 wherein one of $R^2$ and $R^3$ are bound to the ring nitrogen of A.*

*37. A compound of claim 36 wherein $R^2$ is hydrogen and* $R^3$ is bound to the ring nitrogen of A.

*38. A compound of claim 2 wherein A is homopiperazine.*

*39. A method for treating tumors and their metastasis comprising administering a therapeutically effective amount of a compound of claim 23 in combination with one or more chemotherapeutic agents to a patient in need thereof.*

*40. A method for treating tumors and their metastasis comprising administering a therapeutically effective amount of a compound of claim 24 in combination with one or more chemotherapeutic agents to a patient in need thereof.*

* * * * *